（12）United States Patent
Mooney et al.

(10) Patent No.: US 12,427,079 B2
(45) Date of Patent: *Sep. 30, 2025

(54) SYSTEMS AND METHODS FOR A COMPRESSED CONTROLLER FOR AN ACTIVE EXOSKELETON

(71) Applicant: Dephy, Inc., Maynard, MA (US)

(72) Inventors: Luke Mooney, Sudbury, MA (US); Jean-François Duval, Belmont, MA (US)

(73) Assignee: DEPHY, INC., Maynard, MA (US)

( * ) Notice: Subject to any disclaimer, the term of this patent is extended or adjusted under 35 U.S.C. 154(b) by 533 days.

This patent is subject to a terminal disclaimer.

(21) Appl. No.: 17/717,347

(22) Filed: Apr. 11, 2022

(65) Prior Publication Data
US 2022/0409467 A1 Dec. 29, 2022

Related U.S. Application Data

(63) Continuation of application No. 17/028,761, filed on Sep. 22, 2020, now Pat. No. 11,298,287.
(Continued)

(51) Int. Cl.
*A61H 3/00* (2006.01)
*A61H 1/02* (2006.01)
(Continued)

(52) U.S. Cl.
CPC ............ *A61H 3/00* (2013.01); *A61H 1/0266* (2013.01); *G06N 20/00* (2019.01); *G16H 20/30* (2018.01);
(Continued)

(58) Field of Classification Search
None
See application file for complete search history.

(56) References Cited

U.S. PATENT DOCUMENTS 2,477,591 A 8/1949 Follis
2,516,872 A 8/1950 Hauser et al.
(Continued)

FOREIGN PATENT DOCUMENTS

CA 2937610 A1 7/2009
CN 202679044 U 1/2013
(Continued)

OTHER PUBLICATIONS

US Non-Final Office Action on U.S. Appl. No. 17/867,162 dated Apr. 12, 2023 (32 pages).
(Continued)

*Primary Examiner* — Victoria Murphy
*Assistant Examiner* — Savannah L Gabriel
(74) *Attorney, Agent, or Firm* — FOLEY & LARDNER LLP

(57) ABSTRACT

A system to augment motion via a battery-powered active exoskeleton boot is provided. The system can include a controller and an electric motor that generates torque about an axis of rotation of an ankle joint of the user. The controller can receive sensor data associated with activity of the exoskeleton boot during a first time interval. The controller can determine, based on the sensor data input into a model trained via a machine learning technique associated with one or more users performing one or more physical activities, one or more commands for a second time interval. The controller can transmit the one or more commands generated based on the model to the electric motor to cause the electric motor to generate torque about the axis of rotation of the ankle joint of the user in the second time interval.

18 Claims, 16 Drawing Sheets

Related U.S. Application Data

(60) Provisional application No. 63/033,562, filed on Jun. 2, 2020.

(51) Int. Cl.
*G06N 20/00* (2019.01)
*G16H 20/30* (2018.01)

(52) U.S. Cl.
CPC .................. *A61H 2003/007* (2013.01); *A61H 2201/1207* (2013.01); *A61H 2201/1642* (2013.01); *A61H 2201/165* (2013.01); *A61H 2201/501* (2013.01); *A61H 2201/5012* (2013.01); *A61H 2201/5043* (2013.01); *A61H 2201/5046* (2013.01); *A61H 2201/5061* (2013.01); *A61H 2201/5069* (2013.01); *A61H 2201/5084* (2013.01); *A61H 2201/5092* (2013.01)

(56) References Cited

U.S. PATENT DOCUMENTS

| | | | |
|---|---|---|---|
| 2,573,698 | A | 11/1951 | Ellery |
| 3,064,644 | A | 11/1962 | Patterson |
| 5,014,690 | A | 5/1991 | Hepburn et al. |
| 5,490,831 | A | 2/1996 | Myers et al. |
| 5,685,830 | A | 11/1997 | Bonutti |
| 6,299,588 | B1 | 10/2001 | Fratrick |
| 6,872,187 | B1 | 3/2005 | Stark et al. |
| 7,153,242 | B2 | 12/2006 | Goffer |
| 7,431,737 | B2 | 10/2008 | Ragnarsdottir et al. |
| 7,531,006 | B2 | 5/2009 | Clausen et al. |
| 7,628,766 | B1 | 12/2009 | Kazerooni et al. |
| 7,811,333 | B2 | 10/2010 | Jonsson et al. |
| 8,114,168 | B2 | 2/2012 | Olafsson et al. |
| 8,435,309 | B2 | 5/2013 | Gilbert et al. |
| 8,516,918 | B2 | 8/2013 | Jacobsen et al. |
| 8,585,620 | B2 | 11/2013 | McBean et al. |
| 8,597,369 | B2 | 12/2013 | Hansen et al. |
| 8,734,528 | B2 | 5/2014 | Herr et al. |
| 8,764,850 | B2 | 7/2014 | Hansen et al. |
| 8,784,350 | B2 | 7/2014 | Cohen |
| 8,790,282 | B2 | 7/2014 | Jung et al. |
| 8,801,802 | B2 | 8/2014 | Oddsson et al. |
| 8,864,846 | B2 | 10/2014 | Herr et al. |
| 8,870,801 | B2 | 10/2014 | Tomiyama et al. |
| 8,870,967 | B2 | 10/2014 | Herr et al. |
| 9,017,419 | B1 | 4/2015 | Landry et al. |
| 9,066,819 | B2 | 6/2015 | Gramnaes |
| 9,078,774 | B2 | 7/2015 | Jonsson et al. |
| 9,198,821 | B2 | 12/2015 | Unluhisarcikli et al. |
| 9,333,097 | B2 | 5/2016 | Herr et al. |
| 9,339,397 | B2 | 5/2016 | Herr et al. |
| 9,345,608 | B2 | 5/2016 | Phillips |
| 9,351,900 | B2 | 5/2016 | Walsh et al. |
| 9,480,618 | B2 | 11/2016 | Hsiao-Wecksler et al. |
| 9,539,117 | B2 | 1/2017 | Herr et al. |
| 9,554,922 | B2 | 1/2017 | Casler et al. |
| 9,662,262 | B2 | 5/2017 | Hollander et al. |
| 9,693,883 | B2 | 7/2017 | Herr et al. |
| 9,707,104 | B2 | 7/2017 | Clausen |
| 9,737,419 | B2 | 8/2017 | Herr et al. |
| 9,808,390 | B2 | 11/2017 | Caires et al. |
| 9,839,552 | B2 | 12/2017 | Han et al. |
| 9,872,782 | B2 | 1/2018 | Herr et al. |
| 9,907,722 | B2 | 3/2018 | Aguirre-Ollinger et al. |
| 9,925,071 | B2 | 3/2018 | Langlois et al. |
| 9,980,873 | B2 | 5/2018 | Tung et al. |
| 10,195,057 | B2 | 2/2019 | Clausen |
| 10,251,762 | B2 | 4/2019 | Langlois |
| 10,307,271 | B2 | 6/2019 | Holgate et al. |
| 10,307,272 | B2 | 6/2019 | Herr et al. |
| 10,335,294 | B2 | 7/2019 | Huang et al. |
| 10,369,023 | B2 | 8/2019 | Simon et al. |
| 10,405,996 | B2 | 9/2019 | Langlois |
| 10,406,002 | B2 | 9/2019 | Herr et al. |
| 10,426,637 | B2 | 10/2019 | Tong et al. |
| 10,463,561 | B2 | 11/2019 | Zhang et al. |
| 10,485,681 | B2 | 11/2019 | Herr et al. |
| 10,532,000 | B1 | 1/2020 | De Sapio et al. |
| 10,537,449 | B2 | 1/2020 | Han et al. |
| 10,561,563 | B2 | 2/2020 | Herr et al. |
| 10,576,620 | B1 | 3/2020 | Chou et al. |
| 11,389,367 | B2 | 7/2022 | Mooney et al. |
| 11,413,210 | B2 | 8/2022 | Contreras-Vidal et al. |
| 11,752,061 | B2 | 9/2023 | Mooney et al. |
| 11,918,536 | B2 | 3/2024 | Mooney et al. |
| 2006/0167564 | A1 | 7/2006 | Flaherty et al. |
| 2006/0184280 | A1 | 8/2006 | Oddsson et al. |
| 2007/0225620 | A1 | 9/2007 | Carignan et al. |
| 2009/0030530 | A1 | 1/2009 | Martin |
| 2009/0210093 | A1 | 8/2009 | Jacobsen et al. |
| 2009/0222105 | A1 | 9/2009 | Clausen et al. |
| 2010/0049333 | A1 | 2/2010 | Endo et al. |
| 2010/0130894 | A1 | 5/2010 | Ikeuchi |
| 2010/0198124 | A1 | 8/2010 | Bhugra |
| 2010/0231206 | A1 | 9/2010 | Kobayashi |
| 2011/0066088 | A1 | 3/2011 | Little et al. |
| 2012/0089063 | A1 | 4/2012 | Olson et al. |
| 2012/0256381 | A1 | 10/2012 | Bradshaw |
| 2012/0289870 | A1 | 11/2012 | Hsiao-Wecksler et al. |
| 2013/0090580 | A1 | 4/2013 | Hong et al. |
| 2013/0102934 | A1 | 4/2013 | Ikeuchi |
| 2013/0226048 | A1* | 8/2013 | Unluhisarcikli ...... A61H 1/0244 601/34 |
| 2013/0231595 | A1 | 9/2013 | Zoss et al. |
| 2014/0100494 | A1 | 4/2014 | Sarkodie-Gyan et al. |
| 2014/0330431 | A1 | 11/2014 | Hollander et al. |
| 2015/0141878 | A1 | 5/2015 | Roy et al. |
| 2015/0164731 | A1 | 6/2015 | Kwak et al. |
| 2015/0173993 | A1 | 6/2015 | Walsh et al. |
| 2015/0196403 | A1 | 7/2015 | Kim et al. |
| 2015/0257902 | A1 | 9/2015 | Martin |
| 2016/0030201 | A1* | 2/2016 | Zoss ...................... A61H 3/008 623/24 |
| 2016/0107309 | A1 | 4/2016 | Walsh et al. |
| 2016/0143800 | A1* | 5/2016 | Hyung ..................... A61H 3/00 623/32 |
| 2016/0278948 | A1 | 9/2016 | Piercy et al. |
| 2016/0331557 | A1 | 11/2016 | Tong et al. |
| 2016/0331624 | A1 | 11/2016 | Sankai et al. |
| 2017/0043476 | A1* | 2/2017 | Seo ..................... G05B 19/042 |
| 2017/0043482 | A1 | 2/2017 | Hyun et al. |
| 2017/0119132 | A1 | 5/2017 | Pruess et al. |
| 2017/0202724 | A1 | 7/2017 | De Rossi et al. |
| 2017/0354529 | A1 | 12/2017 | Han et al. |
| 2018/0104075 | A1* | 4/2018 | Mooney ................ B25J 9/0006 |
| 2018/0116826 | A1 | 5/2018 | Byars et al. |
| 2018/0125738 | A1 | 5/2018 | Witte et al. |
| 2018/0177665 | A1 | 6/2018 | Rogozinski |
| 2018/0193172 | A1 | 7/2018 | Smith et al. |
| 2018/0200135 | A1 | 7/2018 | Tung et al. |
| 2018/0325764 | A1 | 11/2018 | Yagi |
| 2019/0011743 | A1 | 1/2019 | Yan et al. |
| 2019/0038448 | A1 | 2/2019 | Choi et al. |
| 2019/0065970 | A1 | 2/2019 | Bonutti et al. |
| 2019/0070060 | A1 | 3/2019 | Choi et al. |
| 2019/0083002 | A1* | 3/2019 | Jang ................... A61B 5/02438 |
| 2019/0105215 | A1 | 4/2019 | Dalley et al. |
| 2019/0105777 | A1 | 4/2019 | Dalley et al. |
| 2019/0125004 | A1 | 5/2019 | Thomas et al. |
| 2019/0159728 | A1 | 5/2019 | Pritchard et al. |
| 2019/0159954 | A1* | 5/2019 | Ozsecen ............... B25J 9/0006 |
| 2019/0160321 | A1 | 5/2019 | Ozsecen et al. |
| 2019/0175365 | A1 | 6/2019 | Herr et al. |
| 2019/0183713 | A1 | 6/2019 | Sankai |
| 2019/0254908 | A1 | 8/2019 | Ortlieb et al. |
| 2019/0254909 | A1 | 8/2019 | Lee et al. |
| 2019/0282429 | A1 | 9/2019 | Son et al. |
| 2019/0314185 | A1 | 10/2019 | Yuge et al. |
| 2019/0328552 | A1 | 10/2019 | Herr et al. |
| 2019/0328604 | A1 | 10/2019 | Contreras-Vidal et al. |
| 2019/0343707 | A1 | 11/2019 | Riener et al. |
| 2019/0343710 | A1 | 11/2019 | Lerner |

(56) References Cited

U.S. PATENT DOCUMENTS

| | | | |
|---|---|---|---|
| 2019/0344433 A1 | 11/2019 | Lerner | |
| 2019/0365554 A1 | 12/2019 | Davies-Sekle | |
| 2020/0011406 A1 | 1/2020 | Julin | |
| 2020/0016020 A1 | 1/2020 | Mooney et al. | |
| 2020/0018589 A1 | 1/2020 | Ausserlechner | |
| 2020/0085666 A1 | 3/2020 | Seo et al. | |
| 2020/0093679 A1 | 3/2020 | Sonar et al. | |
| 2020/0160020 A1 | 5/2020 | Cho et al. | |
| 2020/0188214 A1 | 6/2020 | Lee et al. | |
| 2020/0188215 A1* | 6/2020 | Park | A61H 3/00 |
| 2020/0197253 A1 | 6/2020 | Park et al. | |
| 2020/0253772 A1 | 8/2020 | Reid et al. | |
| 2020/0253774 A1 | 8/2020 | Pismennaya et al. | |
| 2020/0276698 A1 | 9/2020 | Ding et al. | |
| 2020/0326780 A1 | 10/2020 | Kearney et al. | |
| 2021/0085554 A1 | 3/2021 | Roh et al. | |
| 2021/0121355 A1 | 4/2021 | Behboodi et al. | |
| 2021/0290470 A1 | 9/2021 | Farris et al. | |
| 2021/0291355 A1 | 9/2021 | Lerner et al. | |
| 2021/0298984 A1 | 9/2021 | Bulea et al. | |
| 2021/0369536 A1 | 12/2021 | Mooney et al. | |
| 2021/0369537 A1 | 12/2021 | Witte et al. | |
| 2021/0370495 A1 | 12/2021 | Swartz et al. | |
| 2021/0393467 A1 | 12/2021 | Ookoba | |
| 2022/0031552 A1 | 2/2022 | Mooney et al. | |
| 2022/0079792 A1 | 3/2022 | Lear et al. | |
| 2022/0110814 A1 | 4/2022 | Mooney et al. | |
| 2022/0273469 A1 | 9/2022 | Kazerooni et al. | |

FOREIGN PATENT DOCUMENTS

| | | |
|---|---|---|
| CN | 105213155 A | 1/2016 |
| CN | 105213153 B | 6/2016 |
| CN | 103813772 B | 7/2016 |
| CN | 104644381 B | 8/2016 |
| CN | 104983543 B | 8/2016 |
| CN | 107115191 A | 9/2017 |
| CN | 107874984 A | 4/2018 |
| CN | 105963100 B | 7/2018 |
| CN | 108283564 A | 7/2018 |
| CN | 108338896 A | 7/2018 |
| CN | 108451748 A | 8/2018 |
| CN | 106491319 B | 12/2018 |
| CN | 105456004 B | 2/2019 |
| CN | 109646245 A | 4/2019 |
| CN | 209107991 U | 7/2019 |
| CN | 209270231 | 8/2019 |
| CN | 110327189 A | 10/2019 |
| CN | 110478191 A | 11/2019 |
| CN | 110575350 A | 12/2019 |
| EP | 2 621 413 B1 | 6/2014 |
| EP | 2 564 817 B1 | 1/2019 |
| IN | 201631013395 A | 10/2017 |
| JP | 5935177 B2 | 6/2016 |
| KR | 101104065 B1 | 1/2012 |
| KR | 20140107029 A | 9/2014 |
| WO | WO-2016/180073 A1 | 1/2016 |
| WO | WO-2016/182473 A1 | 1/2016 |
| WO | WO-2018/023109 A1 | 7/2017 |
| WO | WO-2019/160532 | 2/2018 |
| WO | WO-2019/060791 A1 | 3/2019 |

OTHER PUBLICATIONS

International Preliminary Report on Patentability on PCT Appl. Ser. No. PCT/US2021/047252 dated Mar. 9, 2023 (9 pages).
European Extended Search Report issued in corresponding European Patent Application No. 21817832.5 dated May 29, 2024 (10 pages).
European Extended Search Report issued in corresponding European Patent Application No. 21818627.8 dated May 15, 2024.
Final Office Action on U.S. Appl. No. 17/002,556 DTD Feb. 1, 2024.
Notice of Allowance on U.S. Appl. No. 17/002,556 DTD May 15, 2024.
Partial Supplementary European Search Report issued in corresponding European Patent Application No. 21817291.4 dated May 23, 2024 (11 pages).
US Non-Final Office Action on U.S. Appl. No. 18/238,612 dated Jun. 3, 2024.
US Notice of Allowance on U.S. Appl. No. 17/504,248 dated Nov. 28, 2023 (9 pages).
US Notice of Allowance on U.S. Appl. No. 17/867,162 dated Oct. 30, 2023 (18 pages).
International Preliminary Report on Patentability on PCT Appl. Ser. No. PCT/US2021/047295 dated Mar. 30, 2023 (5 pages).
US Final Office Action on U.S. Appl. No. 17/526,454 dated Apr. 7, 2023 (6 pages).
US Notice of Allowance on U.S. Appl. No. 17/504,261 dated Apr. 7, 2023 (9 pages).
Dollar et al., Active Orthoses for the Lower-Limbs: Challenges and State of the Art, 2008, IEEE, p. 968-977 (Year: 2008).
Dollar et al., Lower Extremity Exoskeletons and Active Orthoses: Challenges and State-of-the-Art, 2008, IEEE, p. 144-158 (Year:2008).
Foreign Action other than Search Report on PCT PCT/US2020/059866 DTD May 27, 2022.
Foreign Search Report on non-Foley case related to PCT PCT/US2021/034086 DTD Jun. 28, 2021.
Foreign Search Report on PCT PCT/US2021/034163 DTD Jun. 25, 2021.
Foreign Search Report on PCT PCT/US2021/034182 DTD Jun. 29, 2021.
Foreign Search Report on PCT PCT/US2021/047295 dated Sep. 23, 2021.
Foreign Search Report on PCT PCT/US2021/34252 DTD Jun. 28, 2021.
Goldfarb et al. Design of a Controlled-Brake Orthosis for FES-aided gait, 1996, IEEE, p. 13-24 (Year:1996).
Haque et al., Design and Preliminary Testing of an Insrumented Exoskeleton for Walking Gait Measurement, 2019, IEEE, 2019, 6 pages.
International Search Report and Written Opinion for PCT Appl. No. PCT/US2021/047252, dated Nov. 23, 2021.
International Search Report and Written Opinion on PCT/US2020/059866 dated Feb. 4, 2021, 8 pages.
Kim et al., Mechanical Design of the Hanyang Exoskeleton Assistive Robot (HEXAR), 2014, IEEE, 479-484 (Year: 2014).
Non-Final Office Action on U.S. Appl. No. 17/028,761 dated Oct. 12, 2021.
Notice of Allowance on U.S. Appl. No. 17/022,982 dated Jan. 29, 2021.
Notice of Allowance on U.S. Appl. No. 17/084,111 dated Feb. 19, 2021.
Notice of Allowance on U.S. Appl. No. 17/084,111 DTD May 20, 2021.
Notice of Allowance on U.S. Appl. No. 17/109,911 dated Feb. 3, 2021.
Notice of Allowance on U.S. Appl. No. 17/136,333 DTD Apr. 6, 2022.
US Non-Final Office Action on U.S. Appl. No. 17/028,761 dated Nov. 23, 2020.
US Notice of Allowance on U.S. Appl. No. 17/022,982 dated Sep. 27, 2021, 9 pages.
US Notice of Allowance on U.S. Appl. No. 17/028,761 dated Feb. 2, 2022.
US Notice of Allowance on U.S. Appl. No. 17/109,911 dated Sep. 14, 2021, 5 pages.
US Notice of Allowance on U.S. Appl. No. 17/109,911 DTD May 25, 2021.
US Notice of Allowance on U.S. Appl. No. 17/084,111 dated Sep. 17, 2021, 7 pages.
US Office Action on U.S. Appl. No. 17/022,982 DTD May 4, 2021.
US Office Action on U.S. Appl. No. 17/028,761 dated Mar. 16, 2021, 18 pages.
US Office Action on U.S. Appl. No. 17/136,333 dated Nov. 23, 2021.

(56) References Cited

OTHER PUBLICATIONS

US Office Action on U.S. Appl. No. 17/136,333 dated Mar. 12, 2021, 24 pages.
US Office Action on U.S. Appl. No. 17/136,333 DTD Jun. 21, 2021.
Witte et al.: "Design of Two Lightweight, High-Bandwidth Torque-Controlled Ankle Exoskeletons" IEEE International Conference on Robotics and Automation (ICRA); May 2015.
Zhang et al.: "Experimental comparison of torque control methods on an ankle exoskeleton during human walking" IEEE International Conference on Robotics and Automation (ICRA); May 2015.
US Corrected Notice of Allowance on U.S. Appl. No. 17/504,261 dated Apr. 24, 2023 (2 pages).
US Notice of Allowance on U.S. Appl. No. 17/526,454 dated Apr. 26, 2023 (8 pages).
European Extended Search Report issued in corresponding European Patent Application No. 21817826.7 dated Jun. 14, 2024 (6 pages).
Office Action issued in corresponding European Patent Application No. 21817291.4 dated Aug. 13, 2024 (10 pages).
Office Action issued in corresponding European Patent Application No. 21862525.9 dated Aug. 26, 2024 (5 pages).
Office Action issued in corresponding European Patent Application No. 21869964.3 dated Aug. 13, 2024 (5 pages).
US Non-Final Office Action on U.S. Appl. No. 18/244,802 dated Aug. 7, 2024 (9 pages).
US Notice of Allowance on U.S. Appl. No. 18/238,612 dated Sep. 11, 2024.
Weerasingha et al., "C-JAE: 3 DOF Robotic Ankle Exoskeleton with Compatible Joint Axes", IEEE, 2018, p. 270-275.
EP Office Action on EP Appl. Ser. No. 20888375.1 dated Sep. 14, 2023 (7 pages).
US Corrected Notice of Allowance on U.S. Appl. No. 17/504,261 dated May 18, 2023 (2 pages).
US Non-Final Office Action on U.S. Appl. No. 17/002,556 dated Aug. 21, 2023 (107 pages).
US Non-Final Office Action on U.S. Appl. No. 17/504,248 dated Jun. 7, 2023 (12 pages).
US Notice of Allowance on U.S. Appl. No. 17/867,162 dated Aug. 30, 2023 (17 pages).
US Notice of Allowance on U.S. Appl. No. 17/867,162 dated Oct. 5, 2023 (18 pages).
International Preliminary Report on Patentability on PCT Appl. Ser. No. PCT/US2021/034086 dated Dec. 15, 2022 (10 pages).
International Preliminary Report on Patentability on PCT Appl. Ser. No. PCT/US2021/034163 dated Dec. 15, 2022 (6 pages).
International Preliminary Report on Patentability on PCT Appl. Ser. No. PCT/US2021/034182 dated Dec. 15, 2022 (5 pages).
International Preliminary Report on Patentability on PCT Appl. Ser. No. PCT/US2021/034252 dated Dec. 15, 2022 (14 pages).
Pirjade et al., "Design and Fabrication of a Low-cost Human Body Lower Limb Exoskeleton," IEEE, Apr. 16, 2020, pp. 32-37.
Sanz-Morere et al., "A Knee-Ankle-Foot Orthosis to Assist the Sound Limb of Transfemoral Amputees," IEEE, vol. 1, No. 1, Feb. 13, 2019, pp. 38-48.
US Non-Final Office Action on U.S. Appl. No. 17/504,261 dated Dec. 20, 2022 (9 pages).
US Non-Final Office Action on U.S. Appl. No. 17/526,454 dated Jan. 12, 2023 (22 pages).
Xie et al., "An Unpowered Flexible Lower Limb Exoskeleton: Walking Assisting and Energy Harvesting," IEEE, vol. 24, No. 5, Oct. 5, 2019, pp. 2236-2247.
Zhou et al., "Preliminary Evaluation of Gait Assistance During Treadmill Walking with a Light-weight Bionic Knee Exoskeleton," IEEE, Dec. 7, 2016, pp. 1173-1178.
US Non-Final Office Action on U.S. Appl. No. 18/594,930 dated Nov. 7, 2024 (78 pages).
US Notice of Allowance on U.S. Appl. No. 18/244,802 dated Dec. 5, 2024.
Office Action issued in corresponding European Patent Application No. 20888375.1 dated Apr. 17, 2025.
US Notice of Allowance on U.S. Appl. No. 18/594,930 dated Apr. 30, 2025.
US Non-Final Office Action on U.S. Appl. No. 17/776,144 dated May 19, 2025.

* cited by examiner

SYSTEMS AND METHODS FOR A COMPRESSED CONTROLLER FOR AN ACTIVE EXOSKELETON

CROSS-REFERENCE TO RELATED APPLICATION

This application claims the benefit of priority under 35 U.S.C. § 120 as a continuation of U.S. patent application Ser. No. 17/028,761, filed Sep. 22, 2020, which claims the benefit of priority under 35 U.S.C. § 119 to U.S. Provisional Application No. 63/033,562, filed on Jun. 2, 2020, each of which is hereby incorporated herein by reference in its entirety.

TECHNICAL FIELD

The present disclosure generally relates to the field of exoskeletons.

BACKGROUND

Exoskeletons can be worn by a user to facilitate movement of limbs of the user.

SUMMARY

At least one aspect of the present disclosure is directed to a system to augment motion via a battery-powered active exoskeleton boot. The system can include a shin pad of an exoskeleton boot to couple to a shin of a user below a knee of the user. The system can include one or more housings enclosing i) a controller comprising memory and one or more processors, and ii) an electric motor that generates torque about an axis of rotation of an ankle joint of the user. In embodiments, at least one of the one or more housings is coupled to the shin pad below the knee of the user. The system can include a battery holder coupled to the shin pad. The battery holder can be configured to receive a battery module. The system can include an output shaft coupled to the electric motor and extending through a bore in a housing of the one or more housings enclosing the electric motor. The controller can receive sensor data associated with activity of the exoskeleton boot during a first time interval. The controller can determine, based on the sensor data input into a model trained via a machine learning technique based on historical motion capture data associated with one or more users performing one or more physical activities, one or more commands for a second time interval subsequent to the first time interval. The controller can transmit the one or more commands generated based on the model to the electric motor to cause the electric motor to generate torque about the axis of rotation of the ankle joint of the user in the second time interval.

In embodiments, the controller can receive, via a network, the model from a command modelling system that trains the model based on the historical motion capture data. The controller can receive historical video data associated with the one or more users performing the one or more physical activities, identify, based on historical video information, one or more torque profiles corresponding to the one or more physical activities and train, using the machine learning technique and based on the one or more torque profiles, the model to cause the model to output the one or more commands responsive to the sensor data.

The system can include a command modelling system. The command modelling system can receive the historical motion capture data comprising historical sensor data, provide, for display via a display device communicatively coupled to the command modelling system, a visual indication of the historical motion capture data, receive, via a user interface, an indication of a torque profile corresponding to the visual indication of the historical motion capture data and train, using the machine learning technique and based on the indication of the torque profile received via the user interface, the model to cause the model to output the one or more commands responsive to the sensor data. The command modelling system can receive the historical motion capture data comprising historical sensor data, provide, for display via a display device communicatively coupled to the command modelling system, a visual indication of the historical motion capture data, receive, via a user interface, an indication of a type of physical activity corresponding to the visual indication of the historical motion capture data and train, using the machine learning technique and based on the indication of the type of physical activity received via the user interface, the model to cause the model to output the one or more commands responsive to the sensor data.

In embodiments, the type of physical activity can include at least one of: walking, running, standing, standing up, or sitting. The one or more physical activities can include at least one of steady state activities or transient activities. The controller can determine the one or more commands for the second time interval to match a torque profile selected based on the sensor data via the model. The command modelling system can receive the historical motion capture data comprising historical sensor data, receive indications of types of physical activities corresponding to the historical motion capture data, and train, using a second machine learning technique and based on the indications of types of physical activities corresponding to the historical motion capture data, a second model to generate a torque profile based on second historical motion capture data.

The command modelling system can receive the second historical motion capture data, determine, based on the second model, one or more torque profiles based on the second historical motion capture data and train the model based on the determined one or more torque profiles and the second historical motion capture data to cause the model to generate the one or more commands based on the sensor data. The historical motion capture data can correspond to data collected via the exoskeleton boot in a plurality of states comprising: an unpowered state, a partially powered state, and a fully powered state.

The controller can receive, via a user interface, input from the user prior to the second time interval and generate, via the model, the one or more commands based on the input and the sensor data. The sensor data can include at least one of ankle joint data, inertial measurement unit data, or battery data. The motion capture data can include at least one of inertial measurement unit data, goniometer data, infrared reflector data, or force plate data.

In at least one aspect, a method of augmenting motion via a battery-powered active exoskeleton boot is provided. The method can include providing a shin pad of an exoskeleton boot for coupling to a shin of a user below a knee of the user. The method can include providing one or more housings enclosing i) a controller comprising memory and one or more processors, and ii) an electric motor that generates torque about an axis of rotation of an ankle joint of the user. In embodiments, at least one of the one or more housings is coupled to the shin pad below the knee of the user. The method can include providing a battery holder coupled to the shin pad, the battery holder to receive a battery module. The method can include providing an output shaft coupled to the electric motor and extending through a bore in a housing of the one or more housings enclosing the electric motor. The method can include receiving, by the controller, sensor data associated with activity of the exoskeleton boot during a first time interval. The method can include determining, by the controller, based on the sensor data input into a model trained via a machine learning technique based on historical motion capture data associated with one or more users performing one or more physical activities, one or more commands for a second time interval subsequent to the first time interval. The method can include transmitting, by the controller, the one or more commands generated based on the model to the electric motor to cause the electric motor to generate torque about the axis of rotation of the ankle joint of the user in the second time interval.

In embodiments, the method can include receiving, by a command modelling system, historical video data associated with the one or more users performing the one or more physical activities. The method can include identifying, by the command modelling system based on the historical video data, one or more torque profiles corresponding to the one or more physical activities. The method can include training, by the command modelling system, using the machine learning technique and based on the one or more torque profiles, the model to cause the model to output the one or more commands responsive to the sensor data. The method can include receiving, by a command modelling system, the historical motion capture data comprising historical sensor data. The method can include providing, by the command modelling system, for display via a display device communicatively coupled to the command modelling system, a visual indication of the historical motion capture data. The method can include receiving, by the command modelling system via a user interface, an indication of a torque profile corresponding to the visual indication of the historical motion capture data. The method can include training, by the command modelling system, using the machine learning technique and based on the indication of the torque profile received via the user interface, the model to cause the model to output the one or more commands responsive to the sensor data.

In embodiments, the method can include receiving, by a command modelling system, the historical motion capture data comprising historical sensor data. The method can include providing, by the command modelling system, for display via a display device communicatively coupled to the command modelling system, a visual indication of the historical motion capture data. The method can include receiving, by the command modelling system via a user interface, an indication of a type of physical activity corresponding to the visual indication of the historical motion capture data. The method can include training, by the command modelling system, using the machine learning technique and based on the indication of the type of physical activity received via the user interface, the model to cause the model to output the one or more commands responsive to the sensor data.

The method can include determining, by the controller, the one or more commands for the second time interval to match a torque profile selected based on the sensor data via the model. The method can include receiving, by the controller via a user interface, input from the user prior to the second time interval. The method can include generating, by the controller via the model, the one or more commands based on the input and the sensor data.

Those skilled in the art will appreciate that the summary is illustrative only and is not intended to be in any way limiting. Other aspects, inventive features, and advantages of the devices and/or processes described herein, as defined solely by the claims, will become apparent in the detailed description set forth herein and taken in conjunction with the accompanying drawings.

BRIEF DESCRIPTION OF THE DRAWINGS

The details of one or more implementations of the subject matter described in this specification are set forth in the accompanying drawings and the description below. Other features, aspects, and advantages of the subject matter will become apparent from the description, the drawings, and the claims.

Like reference numbers and designations in the various drawings indicate like elements.

DETAILED DESCRIPTION

This disclosure relates generally to performance enhancing wearable technologies. Particularly, this disclosure relates to apparatuses, systems, and methods for an active exoskeleton with a local battery. The local battery can include an onboard power source that is used to power electronics and one or more actuators.

I. Exoskeleton Overview

Exoskeletons (e.g., battery-powered active exoskeleton, battery-powered active exoskeleton boot, lower limb exoskeleton, knee exoskeleton, or back exoskeleton) can include devices worn by a person to augment physical abilities. Exoskeletons can be considered passive (e.g., not requiring an energy source such as a battery) or active (e.g., requiring an energy source to power electronics and usually one or many actuators). Exoskeletons may be capable of providing large amounts of force, torque and/or power to the human body in order to assist with motion.

Exoskeletons can transfer energy to the user or human. Exoskeletons may not interfere with the natural range of motion of the body. For example, exoskeletons can allow a user to perform actions (e.g., walking, running, reaching, or jumping) without hindering or increasing the difficulty of performing these actions. Exoskeletons can reduce the difficulty of performing these actions by reducing the energy or effort the user would otherwise exert to perform these actions. Exoskeletons can convert the energy into useful mechanical force, torque, or power. Onboard electronics (e.g., controllers) can control the exoskeleton. Output force and torque sensors can also be used to make controlling easier.

Figure 1:
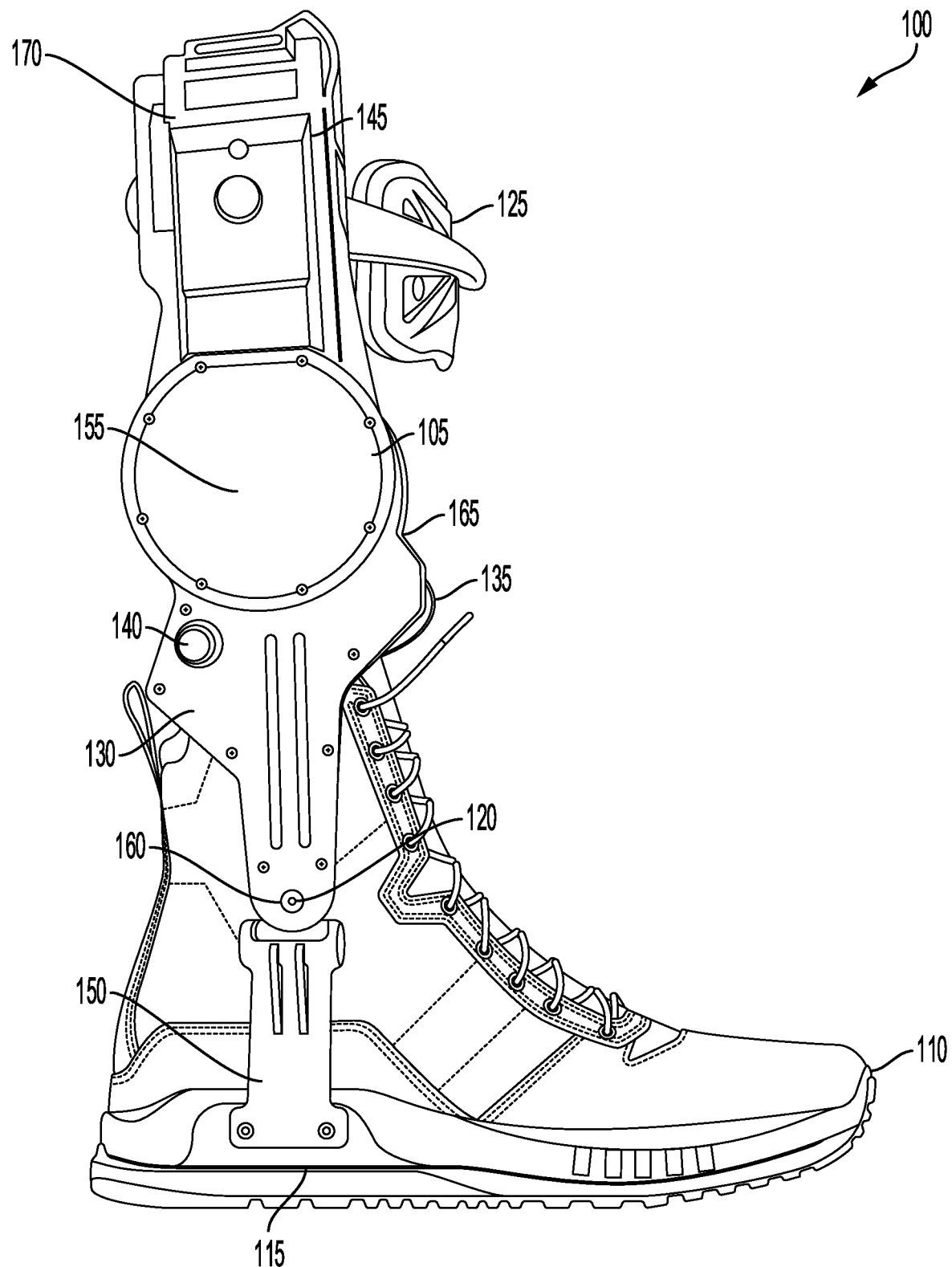
FIG. 1 illustrates a schematic diagram of an exoskeleton, according to an embodiment.

FIG. 1 illustrates a schematic diagram of an exoskeleton 100. The exoskeleton 100 can be referred to as a lower limb exoskeleton, lower limb exoskeleton assembly, lower limb exoskeleton system, ankle exoskeleton, ankle foot orthosis, knee exoskeleton, hip exoskeleton, exoskeleton boot, or exoboot. The exoskeleton 100 can include a water resistant active exoskeleton boot. For example, the exoskeleton 100 can resist the penetration of water into the interior of the exoskeleton 100. The exoskeleton 100 can include a water resistant active exoskeleton boot. For example, the exoskeleton 100 can be impervious to liquids (e.g., water) and non-liquids (e.g., dust, dirt, mud, sand, or debris). The exoskeleton 100 can remain unaffected by water or resist the ingress of water, such as by decreasing a rate of water flow into the interior of the exoskeleton 100 to be less than a target rate indicative of being water resistant or waterproof. For example, the exoskeleton 100 can operate in 3 feet of water for a duration of 60 minutes. The exoskeleton 100 can have an ingress protection rating (IP) rating of 68. The exoskeleton 100 can have a National Electrical Manufacturer Association (NEMA) rating of 4x, which can indicate that the exoskeleton 100 has a degree of protection with respect to harmful effects on the equipment due to the ingress of water (e.g., rain, sleet, snow, splashing water, and hose directed water), and that the exoskeleton can be undamaged by the external formation of ice on the enclosure.

The exoskeleton 100 can include a shin pad 125 (e.g., shin guard). The shin pad 125 can be coupled to a shin of a user below a knee of the user. The shin pad 125 can be coupled to the shin of the user to provide support. The shin pad 125 can include a piece of equipment to protect the user from injury. For example, the shin pad 125 can protect the lower extremities of the user from external impact. The shin pad 125 can interface with the shin of the user. The shin pad 125 can include a band (e.g., adjustable band) configured to wrap around the shin of the user. The shin pad 125 can secure the upper portion of the exoskeleton 100 to the body of the user. The shin pad 125 can secure or help secure the exoskeleton 100 to the shin, leg, or lower limb of the user. The shin pad 125 can provide structural integrity to the exoskeleton 100. The shin pad 125 can support other components of the exoskeleton 100 that can be coupled to the shin pad 125. The shin pad 125 can be made of lightweight, sturdy, and/or water resistant materials. For example, the shin pad 125 can be made of plastics, aluminum, fiberglass, foam rubber, polyurethane, and/or carbon fiber.

The exoskeleton 100 can include one or more housings 105. At least one of the one or more housings 105 can be coupled to the shin pad 125 below the knee of the user. The shin pad 125 can be coupled to the at least one housing via a shin lever. The shin lever can extend from the at least one housing to the shin pad 125. The shin lever can include a mechanical structure that connects the shin pad 125 to a chassis. The chassis can include a mechanical structure that connects static components.

The one or more housings 105 can enclose electronic circuitry (e.g., electronic circuitry 505). The one or more housings 105 can encapsulate some or all the electronics of the exoskeleton 100. The one or more housings 105 can include an electronics cover (e.g., case). The one or more housings 105 can enclose an electric motor (e.g., motor 330). The electric motor can generate torque about an axis of rotation of an ankle joint of the user. The ankle joint can allow for dorsiflexion and/or plantarflexion of the user's foot. The exoskeleton 100 can include an ankle joint component 120 that rotates about the axis of rotation the ankle joint. The ankle joint component 120 can be positioned around or adjacent to the ankle joint.

The exoskeleton 100 can include a rotary encoder 155 (e.g., shaft encoder, first rotary encoder, or motor encoder). The rotary encoder 155 can be enclosed within the one or more housings 105. The rotary encoder 155 can measure an angle of the electric motor. The angle of the electric motor can be used by the controller to determine an amount of torque applied by the exoskeleton 100. For example, the angle of the electric motor can correspond to an amount of torque applied by the exoskeleton 100. An absolute angle of the electric motor can correspond to an amount of torque applied by the exoskeleton 100. The rotary encoder 155 can include an inductive encoder. The ankle joint component 120 can be actuated by a motor (e.g., electric motor). The rotary encoder 155 can include a contactless magnetic encoder or an optical encoder.

The exoskeleton 100 can include a second rotary encoder 160 (e.g., ankle encoder). The second rotary encoder 160 can measure an angle of the ankle joint. The angle of the ankle joint can be used by the controller to determine an amount of torque applied by the exoskeleton 100. The second rotary encoder 160 can include a first component enclosed in the one or more housings 105 and in communication with the electronic circuitry 505. The second rotary encoder 160 can include a second component located outside the one or more housings 105 and configured to interact with the first component. The second rotary encoder 160 can include a contactless magnetic encoder, a contactless inductive encoder, or an optical encoder. The second rotary encoder 160 can detect the angle of the ankle joint while the rotary encoder 155 can detect the angle of the electric motor. The angle of the electric motor can be different from the angle of the ankle joint. The angle of the electric motor can be independent of the angle of the ankle joint. The angle of the ankle joint can be used to determine an output (e.g., torque) of the electric motor. The ankle joint component 120 can be coupled to the second rotary encoder 160.

The one or more housings 105 can encapsulate electronics that are part of the exoskeleton 100. The one or more housings 105 can form a fitted structure (e.g., clamshell structure) to enclose the electronic circuitry and the electric motor. The fitted structure can be formed from two or more individual components. The individual components of the fitted structure can be joined together to form a single unit. The one or more housings 105 can be formed of plastic or metal (e.g., aluminum). An adhesive sealant can be placed between individual components of the fitted structure and under the electronics cover. A gasket can be placed between individual components of the fitted structure and under the electronics cover. The gasket can be placed in the seam between the individual components of the fitted structure.

A sealant 165 can be placed in contact with the one or more housings 105 to close the one or more housings 105 and prevent an ingress of water into the one or more housings 105. The sealant 165 used to close the one or more housings 105 can include an adhesive sealant (e.g., super glue, epoxy resin, or polyvinyl acetate). The adhesive sealant can include a substance used to block the passage of fluids through the surface or joints of the one or more housings 105. The sealant 165 used to close the one or more housings 105 can include epoxy. The sealant 165 can permanently seal or close the one or more housings 105. For example, the sealant 165 can seal or close the one or more housings 105 such that the one or more housings are not removably attached to one another.

The exoskeleton 100 can couple with a boot 110. For example, the exoskeleton 100 can be attached to the boot 110. The boot 110 can be worn by the user. The boot 110 can be connected to the exoskeleton 100. The exoskeleton 100 can be compatible with different boot shapes and sizes.

The exoskeleton 100 can include an actuator 130 (e.g., actuator lever arm, or actuator module). The actuator 130 can include one or more of the components in the exoskeleton 100. For example, the actuator 130 can include the one or more housings 105, the footplate 115, the ankle joint component 120, the actuator belt 135, and the post 150, while excluding the boot 110. The boot 110 can couple the user to the actuator 130. The actuator 130 can provide torque to the ground and the user.

The exoskeleton 100 can include a footplate 115 (e.g., carbon insert, carbon shank). The footplate 115 can include a carbon fiber structure located inside of the sole of the boot 110. The footplate 115 can be made of a carbon-fiber composite. The footplate 115 can be inserted into the sole of the boot 110. The footplate 115 can be used to transmit torque from the actuator 130 to the ground and to the user. The footplate 115 can be located in the sole of the exoskeleton 100. This footplate 115 can have attachment points that allow for the connection of the exoskeleton's mechanical structure. An aluminum insert with tapped holes and cylindrical bosses can be bonded into the footplate 115. This can create a rigid mechanical connection to the largely compliant boot structure. The bosses provide a structure that can be used for alignment. The footplate 115 can be sandwiched between two structures, thereby reducing the stress concentration on the part. This design can allow the boot to function as a normal boot when there is no actuator 130 attached.

The exoskeleton 100 can include an actuator belt 135 (e.g., belt drivetrain). The actuator belt 135 can include a shaft that is driven by the motor and winds the actuator belt 135 around itself. The actuator belt 135 can include a tensile member that is pulled by the spool shaft and applies a force to the ankle lever. Tension in the actuator belt 135 can apply a force to the ankle lever. The exoskeleton 100 can include an ankle lever. The ankle lever can include a lever used to transmit torque to the ankle. The exoskeleton 100 can be used to augment the ankle joint.

The exoskeleton 100 can include a power button 140 (e.g., switch, power switch). The power button 140 can power the electronics of the exoskeleton 100. The power button 140 can be located on the exterior of the exoskeleton 100. The power button 140 can be coupled to the electronics in the interior of the exoskeleton 100. The power button 140 can be electrically connected to an electronic circuit. The power button 140 can include a switch configured to open or close the electronic circuit. The power button 140 can include a low-power, momentary push-button configured to send power to a microcontroller. The microcontroller can control an electronic switch.

The exoskeleton 100 can include a battery holder 170 (e.g., charging station, dock). The battery holder 170 can be coupled to the shin pad 125. The battery holder 170 can be located below the knee of the user. The battery holder 170 can be located above the one or more housings 105 enclosing the electronic circuitry. The exoskeleton 100 can include a battery module 145 (e.g., battery). The battery holder 170 can include a cavity configured to receive the battery module 145. A coefficient of friction between the battery module 145 and the battery holder 170 can be established such that the battery module 145 is affixed to the battery holder 170 due to a force of friction based on the coefficient of friction and a force of gravity. The battery module 145 can be affixed to the battery holder 170 absent a mechanical button or mechanical latch. The battery module 145 can be affixed to the battery holder 170 via a lock, screw, or toggle clamp. The battery holder 170 and the battery module 145 can be an integrated component (e.g., integrated battery). The integrated battery can be supported by a frame of the exoskeleton 100 as opposed to having a separated enclosure. The integrated battery can include a charging port. For example, the charging port can include a barrel connector or a bullet connector. The integrated battery can include cylindrical cells or prismatic cells.

The battery module 145 can power the exoskeleton 100. The battery module 145 can include one or more electrochemical cells. The battery module 145 can supply electric power to the exoskeleton 100. The battery module 145 can include a power source (e.g., onboard power source). The power source can be used to power electronics and one or more actuators. The battery module 145 can include a battery pack. The battery pack can be coupled to the one or more housings 105 below a knee of the user. The battery pack can include an integrated battery pack. The integrated battery pack can remove the need for power cables, which can reduce the snag hazards of the system. The integrated battery pack can allow the system to be a standalone unit mounted to the user's lower limb. The battery module 145 can include a battery management system 324 to perform various operations. For example, the system can optimize the energy density of the unit, optimize the longevity of the cells, and enforce safety protocols to protect the user.

The battery module 145 can include a removable battery. The battery module 145 can be referred to as a local battery because it is located on the exoboot 100 (e.g., on the lower limb or below the knee of the user), as opposed to located on a waist or back of the user. The battery module 145 can include a weight-mounted battery, which can refer to the battery being held in place on the exoboots 100 via gravity and friction, as opposed to a latching mechanism. The battery module 145 can include a water resistant battery or a waterproof battery. The exoskeleton 100 and the battery module 145 can include water resistant connectors.

The battery module 145 can include a high-side switch (e.g., positive can be interrupted). The battery module 145 can include a ground that is always connected. The battery module 145 can include light emitting diodes (LEDs). For example, the battery module 145 can include three LEDs used for a user interface. The LEDs can be visible from one lens so that the LEDs appear as one multicolor LED. The LEDs can blink in various patterns and/or colors to communicate a state of the battery module 145 (e.g., fully charged, partially charged, low battery, or error).

The exoskeleton 100 can include a post 150. The post 150 can include a mechanical structure that connects to the boot 110. The post 150 can couple the ankle joint component 120 with the footplate 115. The post 150 can be attached at a first end to the footplate 115. The post 150 can be attached at a second end to the ankle joint component 120. The post 150 can pivot about the ankle joint component 120. The post 150 can include a mechanical structure that couples the footplate 115 with the ankle joint component 120. The post 150 can include a rigid structure. The post 150 can be removably attached to the footplate 115. The post 150 can be removably attached to the ankle joint component 120. For example, the post 150 can be disconnected from the ankle joint component 120.

The exoskeleton 100 can include a rugged system used for field testing. The exoskeleton 100 can include an integrated ankle lever guard (e.g., nested lever). The exoskeleton 100 can include a mechanical shield to guard the actuator belt 135 and ankle lever transmission from the environment. The housing structure of the system can extend to outline the range of travel of the ankle lever (e.g., lever arm 1140) on the lateral and medial side.

II. Active Exoskeleton with Local Battery

Exoskeletons 100 can transform an energy source into mechanical forces that augment human physical ability. Exoskeletons 100 can have unique power requirements. For example, exoskeletons 100 can use non-constant power levels, such as cyclical power levels with periods of high power (e.g., 100 to 1000 Watts) and periods of low or negative power (e.g., 0 Watts). Peaks in power can occur once per gait cycle. Batteries configured to provide power to the exoskeleton 100 can be the source of various issues. For example, batteries located near the waist of a user can require exposed cables that extend from the battery to the lower limb exoskeleton. These cables can introduce snag hazards, make the device cumbersome, and add mass to the system. Additionally, long cables with high peak power can result in excess radio emissions and higher voltage drops during high current peaks. Thus, systems, methods and apparatus of the present technical solution provide an exoskeleton with a local battery that can perform as desired without causing snag hazards, power losses, and radio interference. Additionally, the battery can be located close to the knee such that the mass felt by the user is reduced as compared to a battery located close the foot of the user.

Figure 2:
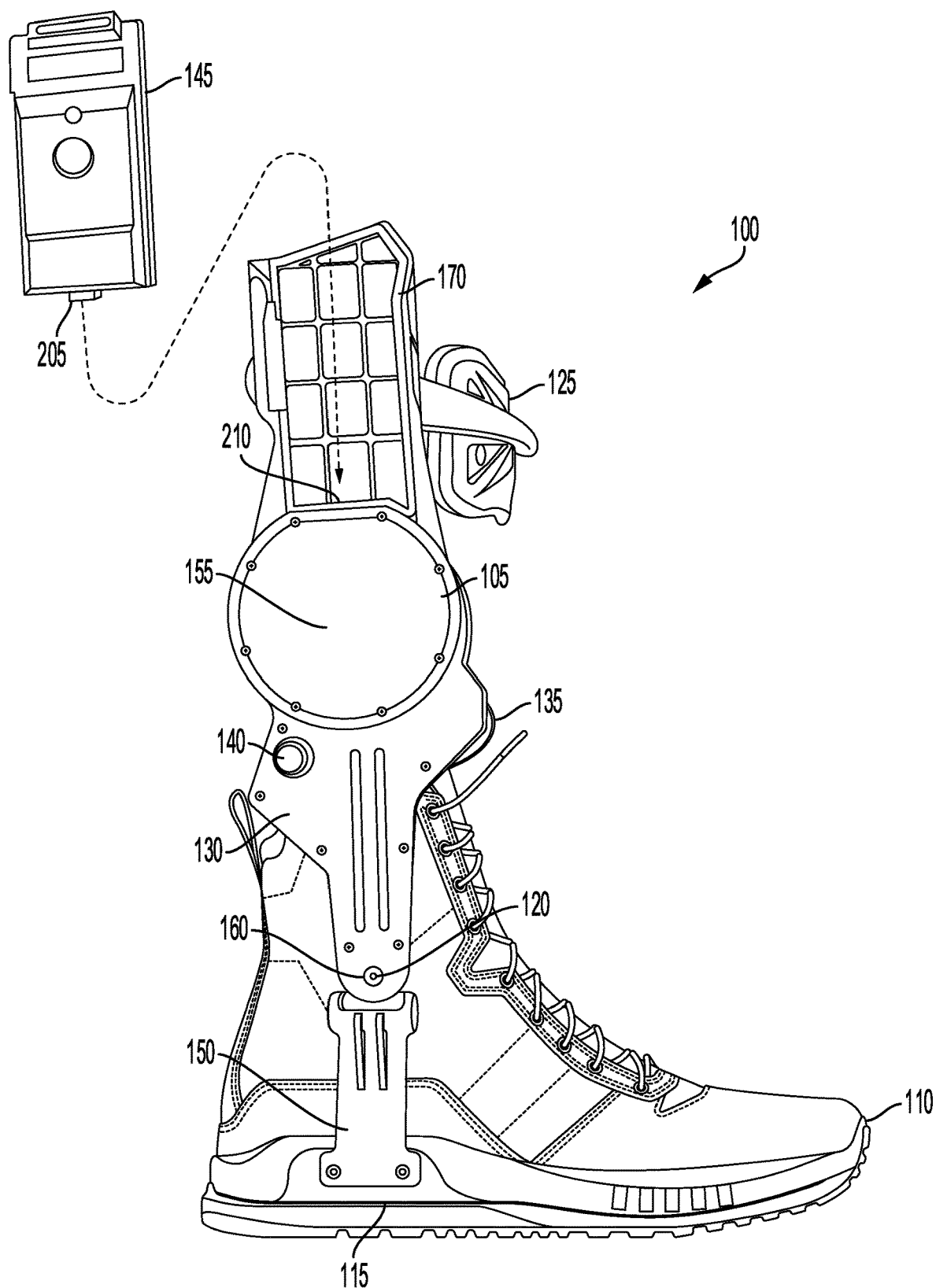
FIG. 2 illustrates a schematic diagram of an exoskeleton, according to an embodiment.

FIG. 2 illustrates a schematic diagram of the exoskeleton 100. The exoskeleton 100 includes the one or more housings 105, the boot 110 the footplate 115, the ankle joint component 120, shin pad 125, the actuator 130, the actuator belt 135, the power button 140, the battery module 145, the post 150, the rotary encoder 155, and the second rotary encoder 160. The battery module 145 can be inserted into the exoskeleton 100. The battery module 145 can include a sealed battery. The battery module 145 can coupled with the exoskeleton 100 via a waterproof or water resistant connection. The battery module 145 can connect locally (e.g., proximate) to the exoskeleton 100 such that a wire is not needed to run from the battery module 145 to the electronics.

The battery module 145 can be removably affixed to the battery holder 170. For example, the battery module 145 can slide in and out of the battery holder 170. By removably affixing the battery module 145 to the battery holder 170, the battery module 145 can be replaced with another battery module 145, or the battery module 145 can be removed for charging. The battery module 145 can include a first power connector 205 that electrically couples to a second power connector 210 located in the battery holder 170 while attached to the battery holder 170 to provide electric power to the electronic circuitry and the electric motor. The first power connector 205 and the second power connector 210 can couple (e.g., connect) the battery module 145 with the electronic circuitry. The first power connector 205 and the second power connector 210 can couple the battery module 145 with the one or more housings 105. The first power connector 205 can be recessed in the battery module 145 to protect the first power connector 205 from loading and impacts. The first power connector 205 and the second power connector 210 can include wires (e.g., two wires, three wires, or four wires). The battery module 145 can communicate with the electronic circuitry via the first power connector 205 and the second power connector 210. The first power connector 205 and the second power connector 210 can include an exposed connector.

The geometry of the battery module 145 can allow for storage and packing efficiency. The battery module 145 can include a gripping element to allow for ergonomic ease of removal and insertion of the battery module 145 into the battery holder 170. The battery module 145 can be made of lightweight plastics or metals. The battery module 145 can be made of heat insulating materials to prevent heat generated by the battery cells 305 from reaching the user. One or more faces of the battery module 145 can be made of metal to dissipate heat.

The exoskeleton 100 can communicate with the battery module 145 during operation. The exoskeleton 100 can use battery management system information to determine when safety measures will trigger. For example, during a high current peak (e.g., 15 A) or when the temperature is near a threshold, the power output can be turned off. The exoskeleton 100 can temporarily increase safety limits for very specific use cases (e.g., specific environmental conditions, battery life). The battery module 145 can prevent the exoskeleton 100 from shutting down by going into a low power mode and conserving power. The exoskeleton 100 can put the battery module 145 in ship mode if a major error is detected and the exoskeleton 100 wants to prevent the user from power cycling. The battery management system 324 can be adapted to support more or less series cells, parallel cells, larger capacity cells, cylindrical cells, different lithium chemistries, etc.

Figure 3:
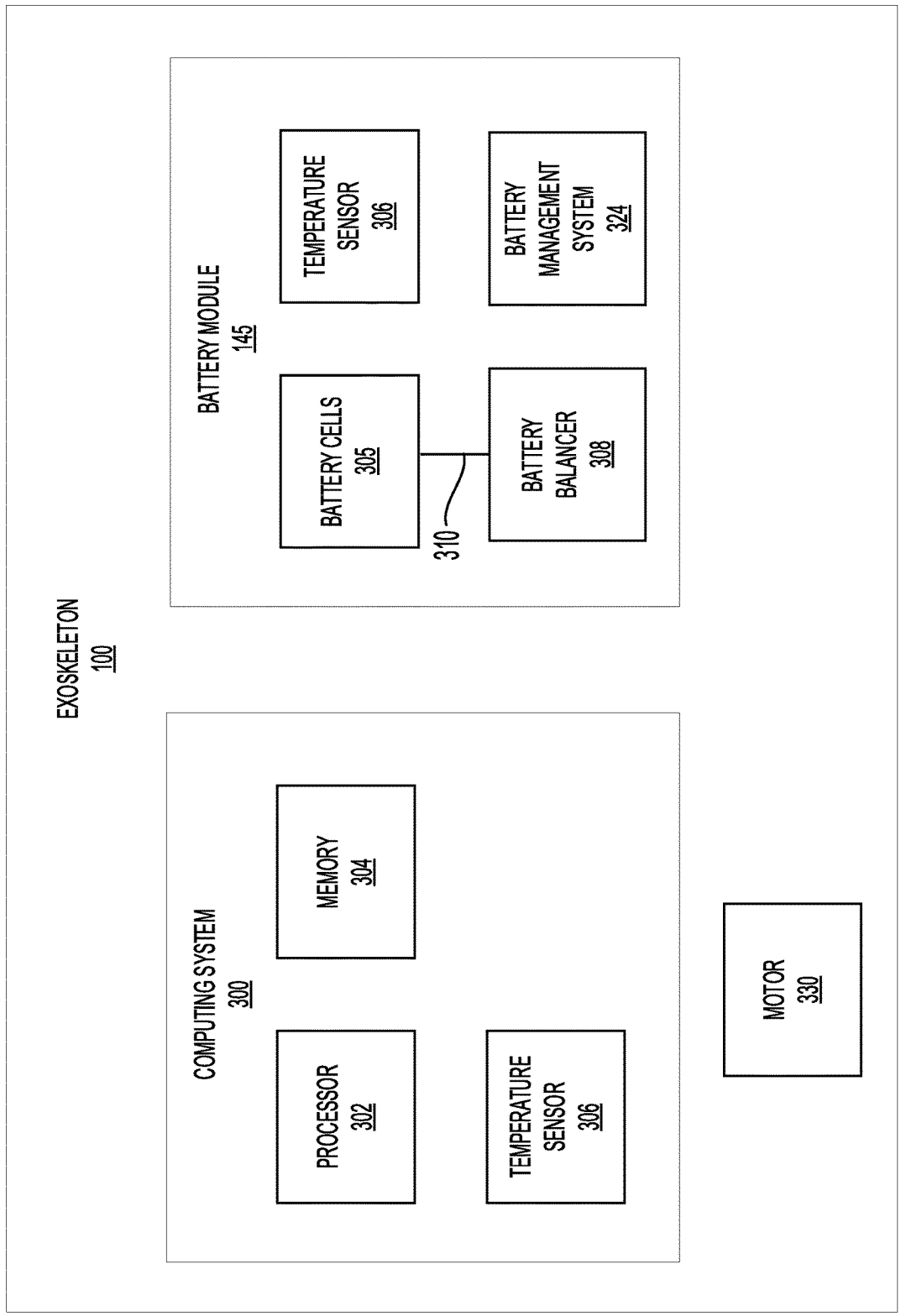
FIG. 3 illustrates a schematic diagram of an exoskeleton, according to an embodiment.

FIG. 3 illustrates a schematic diagram of an exoskeleton 100. The exoskeleton 100 can include a motor 330. The motor 330 can generate torque about an axis of rotation of an ankle joint of the user. The exoskeleton 100 can include the battery module 145. The exoskeleton 100 can include a computing system 300. The exoskeleton 100 can include one or more processors 302, memory 304, and one or more temperature sensors 106 (e.g., thermocouples). The one or more processors 302, memory 304, and one or more temperature sensor 106 can be located within the computing system 300. In some cases, the computing system 300 can include the batter balancer 308 as opposed to the battery module 145.

The one or more processors 302 can receive data corresponding to a performance of the battery module 145. The data can include one or more of a temperature, current, voltage, battery percentage, internal state or firmware version. The one or more processors 302 can determine, based on a safety policy, to trigger a safety action. The safety policy can include triggering the safety action if a threshold temperature, voltage or battery percentage is crossed. For example, the safety policy can include triggering the safety action if a temperature of one or more of the plurality of battery cells 305 is higher than a threshold temperature. The safety policy can include triggering the safety action if a battery percentage of the battery module 145 is below a threshold battery percentage. The safety policy can include triggering the safety action if a measured temperature is higher than the threshold temperature. The measured temperature can include the temperature of the printed circuit board and battery cells 305. The measured temperature can include the temperature of the printed circuit board and battery cells 305 measured in two locations. The safety policy can include triggering the safety action if a measured voltage is higher than the threshold voltage.

The one or more processors 302 can instruct, based on the safety action, the electronic circuitry to adjust delivery of power from the battery module 145 to the electric motor to reduce an amount of torque generated about the axis of rotation of the ankle joint of the user. The safety action can include lowering or reducing the amount of torque generated about the axis of rotation of the ankle joint of the user. The safety action can include increasing the amount of torque generated about the axis of rotation of the ankle joint of the user.

The one or more temperature sensors 306 can be placed between the plurality of battery cells 305 to provide an indication of a temperature between the plurality of battery cells 305. A temperature sensor of the one or more temperature sensors 306 can be mounted on the printed circuit board to measure a temperature of the printed circuit board. The electronic circuitry 505 can control the delivery of power from the battery module 145 to the electric motor based at least in part on the indication of the temperature between the plurality of battery cells 305 or the temperature of the printed circuit board.

The one or more battery balancers 308 can be configured to actively transfer energy from a first battery cell 305 of the plurality of battery cells 305 to a second battery cell 305 of the plurality of battery cells 305 having less charge than the first battery cell 305. A signal trace 1210 can electrically connect the plurality of battery cells 305 to the one or more battery balancers 308. The signal trace 1210 can be located on the printed circuit board.

The exoskeleton 100 can include the battery module 145. The battery module 145 can include a plurality of battery cells 305, one or more temperature sensors 306, one or more battery balancers 308, and a battery management system 324. The battery management system 324 can perform various operations. For example, the battery management system 324 can optimize the energy density of the unit, optimize the longevity of the cells 305, and enforce the required safety to protect the user. The battery management system 324 can go into ship mode by electrically disconnecting the battery module 145 from the rest of the system to minimize power drain while the system is idle. The battery management system 324 can go into ship mode if a major fault is detected. For example, if one or more of the plurality of battery cells 305 self-discharge at a rate higher than a threshold, the battery management system 324 can re-enable the charging port.

While these components are shown as part of the exoskeleton 100, they can be located in other locations such as external to the exoskeleton 100. For example, the battery management system 324 or the computing system 300 can be located external to the exoskeleton 100 for testing purposes.

Figure 4:
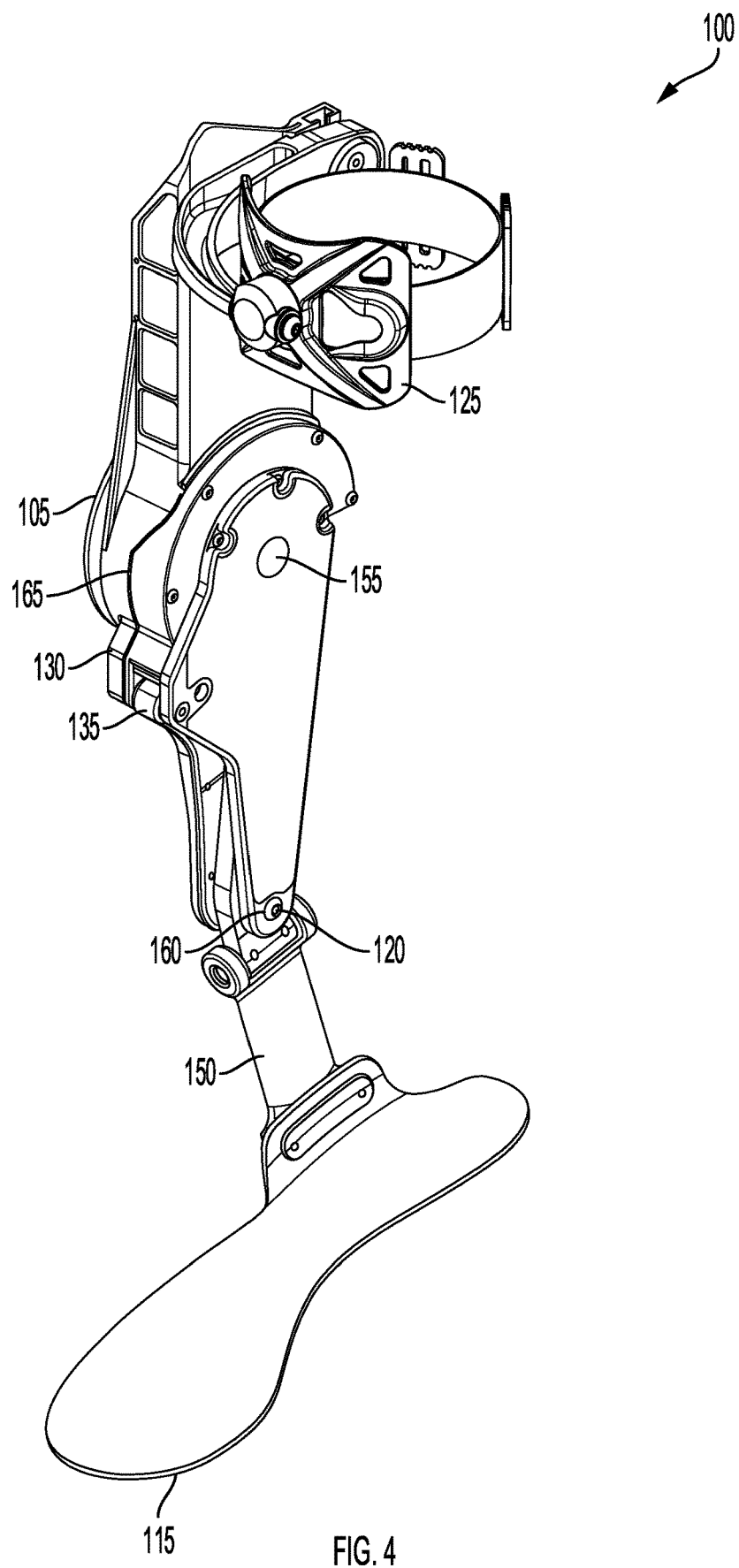
FIG. 4 illustrates a schematic diagram of an exoskeleton, according to an embodiment.

FIG. 4 illustrates a schematic diagram of the exoskeleton 100. The exoskeleton 100 can include the one or more housings 105, the footplate 115, the ankle joint component 120, shin pad 125, the actuator 130, the actuator belt 135, the post 150, the rotary encoder 155, the second rotary encoder 160, and the sealant 165 as described above. The one or more housings 105 can be coupled to the shin pad 125. The post 150 can couple the ankle joint component 120 with the footplate 115. The actuator 130 can include the one or more housings 105, the footplate 115, the ankle joint component 120, the actuator belt 135, and the post 150. The rotary encoder 155 can measure an angle of the electric motor. The second rotary encoder 160 can measure an angle of the ankle joint. The sealant 165 can be placed in contact with the one or more housings 105 to close the one or more housings 105 and prevent an ingress of water into the one or more housings 105.

Figure 5:
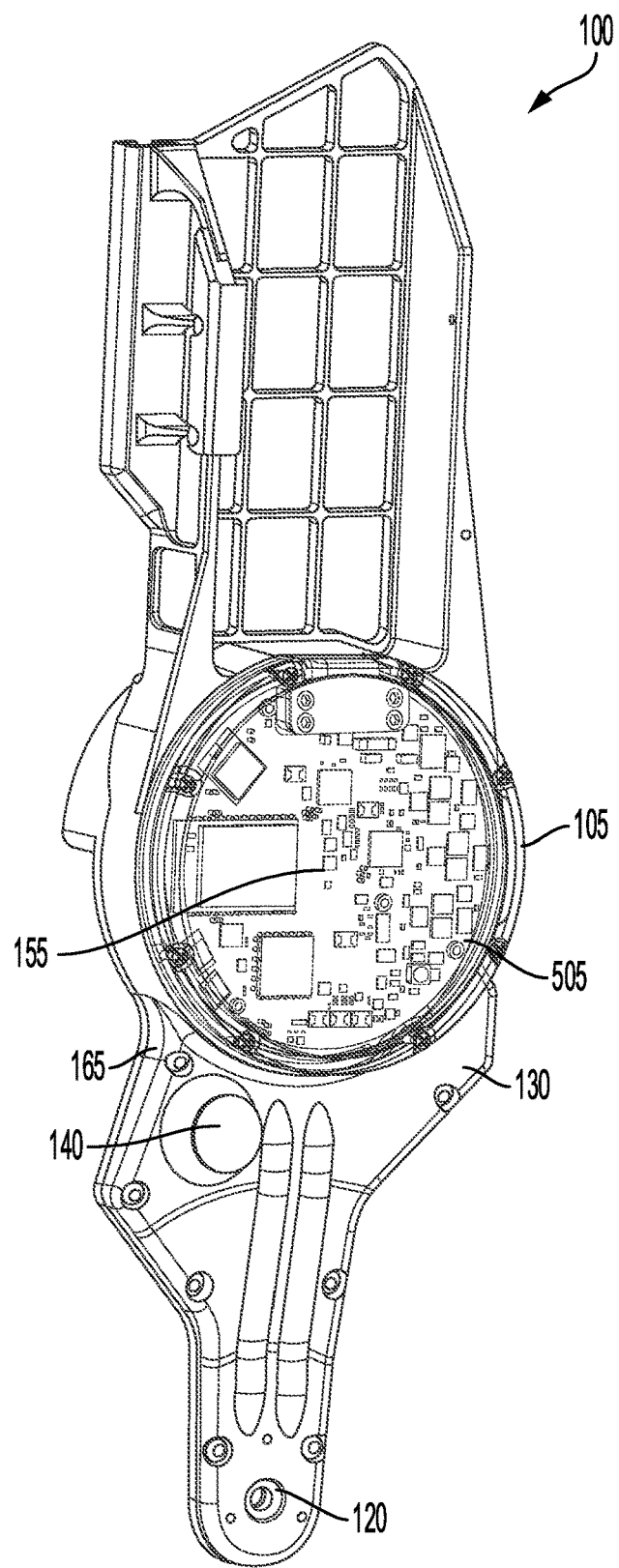
FIG. 5 illustrates a schematic diagram of the exoskeleton and internal parts, according to an embodiment.

FIG. 5 illustrates a schematic diagram of the exoskeleton 100 and internal parts. The exoskeleton 100 can include the one or more housings 105, the ankle joint component 120, the actuator 130, the power button 140, the rotary encoder 155, the second rotary encoder 160, and the sealant 165 as described above. The internal parts can include electronic circuitry 505 (e.g., electronic circuit, circuitry, electronics). The electronic circuitry 505 can include individual electronic components (e.g., resistors, transistors, capacitors, inductors, diodes, processors, or controllers). The power button 140 can be electrically connected to the electronic circuitry 505. The electronic circuitry 505 can be located behind the electric motor. The electronic circuitry 505 can include the main electronics board. The rotary encoder 155 can be located between the motor and electronic circuitry 505. The electronic circuitry 505 can control delivery of power from the battery module 145 to the electric motor to generate torque about the axis of rotation of the ankle joint of the user.

Figure 6:
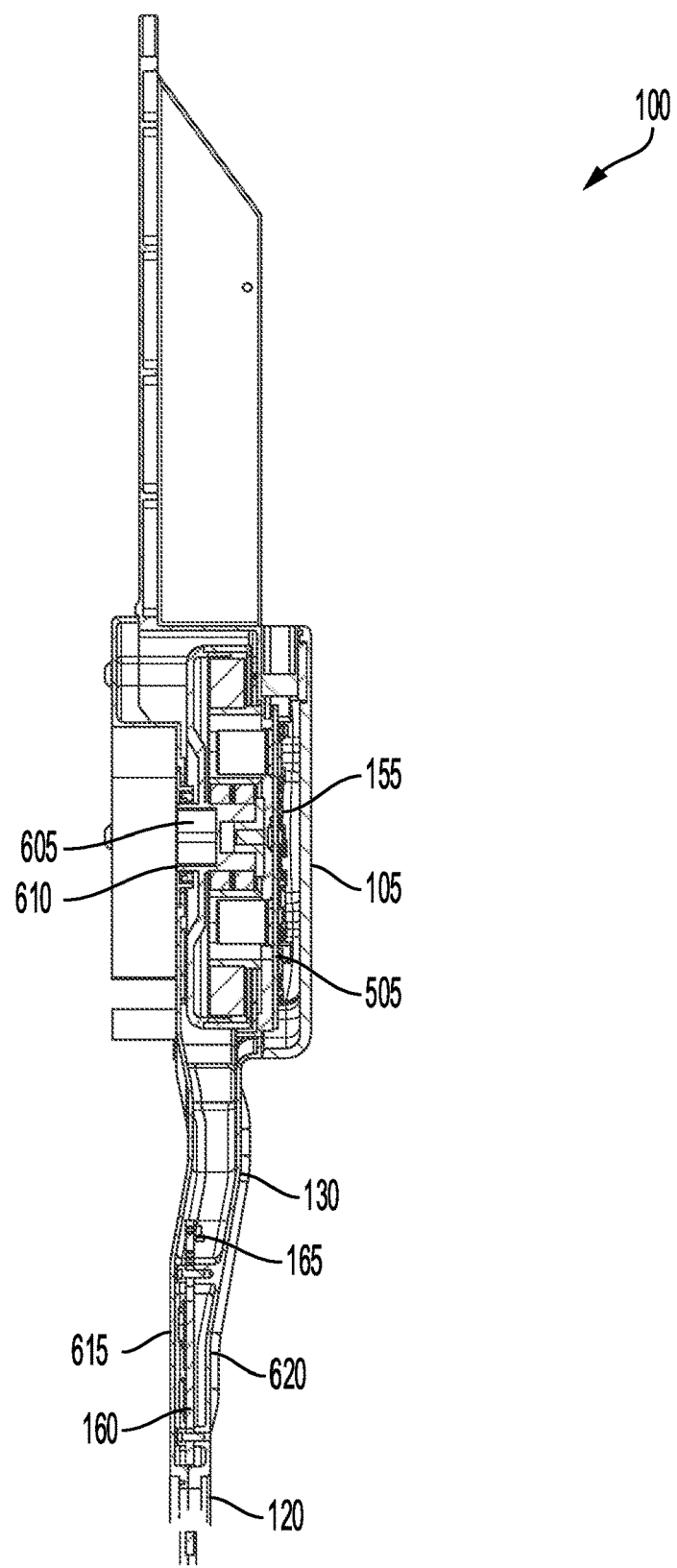
FIG. 6 illustrates a side view of an exoskeleton, according to an embodiment.

FIG. 6 illustrates a side view of the exoskeleton 100. The exoskeleton 100 can include the one or more housings 105, ankle joint component 120, the actuator 130, the rotary encoder 155, the second rotary encoder 160, the sealant 165, and electronic circuitry 505 as described above. The exoskeleton 100 can include an output shaft 605 (e.g., motor rotor, spool shaft, pinion gear, spur gear, or toothed pulley). The output shaft 605 can be coupled to the electric motor. The output shaft 605 can extend through a bore 610 in a housing of the one or more housings 105 enclosing the electric motor. The bore 610 can receive the output shaft 605. An encoder chip can be located on the electronics board on a first side of the electric motor. The encoder chip can measure the angular position of the rotary encoder 155. The exoskeleton 100 can include a transmission (e.g., gearbox) configured to couple the output shaft 605 to the electric motor. The transmission can include a machine in a power transmission system. The transmission can provide controlled application of power. The output shaft 605 can be integrated into the motor rotor. The output shaft 605 can be part of a mechanism (e.g., gears, belts, linkage, or change). An ankle shaft can extend through the second rotary encoder 160 which can increase the structural integrity of the exoskeleton 100.

The exoskeleton 100 can include a first component of the fitted structure 615 (e.g., first clamshell structure). The exoskeleton 100 can include a second component of the fitted structure 620 (e.g., second clamshell structure). The first component of the fitted structure 615 can be coupled with the second component of the fitted structure 620. The first component of the fitted structure 615 can be attached to the second component of the fitted structure 620 via the sealant 165 (e.g., adhesive sealant). The first component of the fitted structure 615 can be coupled to the second component of the fitted structure 620 such that the fitting prevents or decreases a rate of water flow into the interior of the exoskeleton 100. The fitted structure can include two or more components such that the assembly components prevents or decreases a rate of water flow into the interior of the exoskeleton 100. The first component of the fitted structure 615 and the second component of the fitted structure 620 can be stationary components. The number of individual components of the fitted structure can be minimized to decrease the number of possible entry points for water to enter the exoskeleton 100. The possible entry points can include seams and/or moving parts of the exoskeleton 100. The seams can be permanently sealed via the sealant 165.

An adhesive sealant (e.g., super glue, epoxy resin, or polyvinyl acetate) can be placed between the first component of the fitted structure 615 and the second component of the fitted structure 620. The adhesive sealant can prevent or decrease the rate of water flow through the seam between the first component of the fitted structure 615 and the second component of the fitted structure 620 into the interior of the exoskeleton 100. The adhesive sealant can be placed under the electronics cover. The adhesive sealant can prevent or decrease the rate of water flow through the seam between the electronics cover and the exoskeleton one or more housings 105 into the interior of the exoskeleton 100.

A gasket can be placed between the first component of the fitted structure 615 and the second component of the fitted structure 620. The gasket can be placed in the seam between the first component of the fitted structure 615 and the second component of the fitted structure 620. The gasket can prevent or decrease the rate of water flow through the seam between the first component of the fitted structure 615 and the second component of the fitted structure 620.

Figure 7:
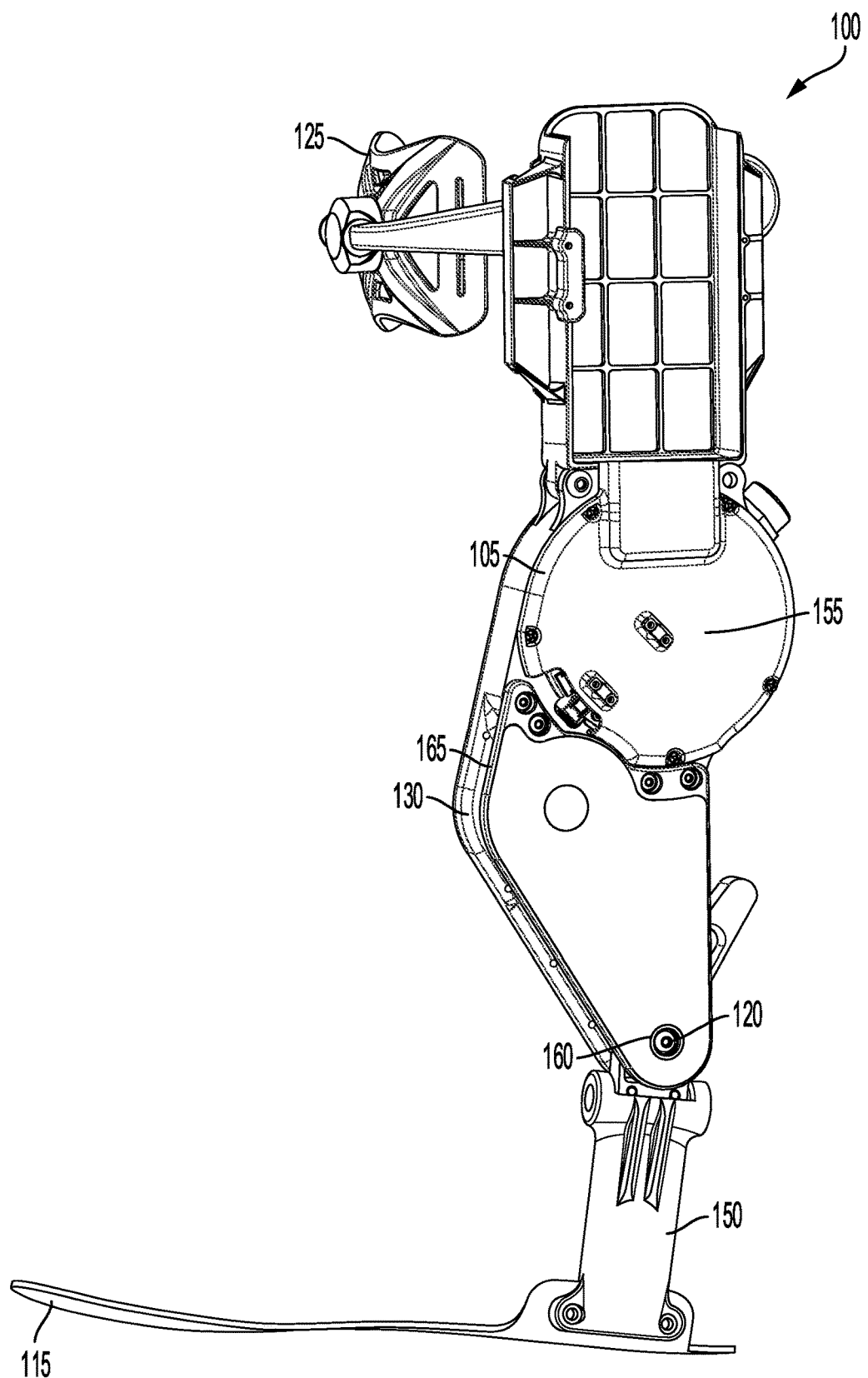
FIG. 7 illustrates a schematic diagram of an exoskeleton, according to an embodiment.

FIG. 7 illustrates a schematic diagram of the exoskeleton 100. The exoskeleton 100 can include the one or more housings 105, the footplate 115, the ankle joint component 120, the shin pad 125, the actuator 130, the post 150, the rotary encoder 155, the second rotary encoder 160, and the sealant 165 as described above. The one or more housings 105 can be coupled to the shin pad 125. The post 150 can couple the ankle joint component 120 with the footplate 115. The actuator 130 can include the one or more housings 105, the footplate 115, the ankle joint component 120, and the post 150. The rotary encoder 155 can measure an angle of the electric motor. The second rotary encoder 160 can measure an angle of the ankle joint.

Figure 8:
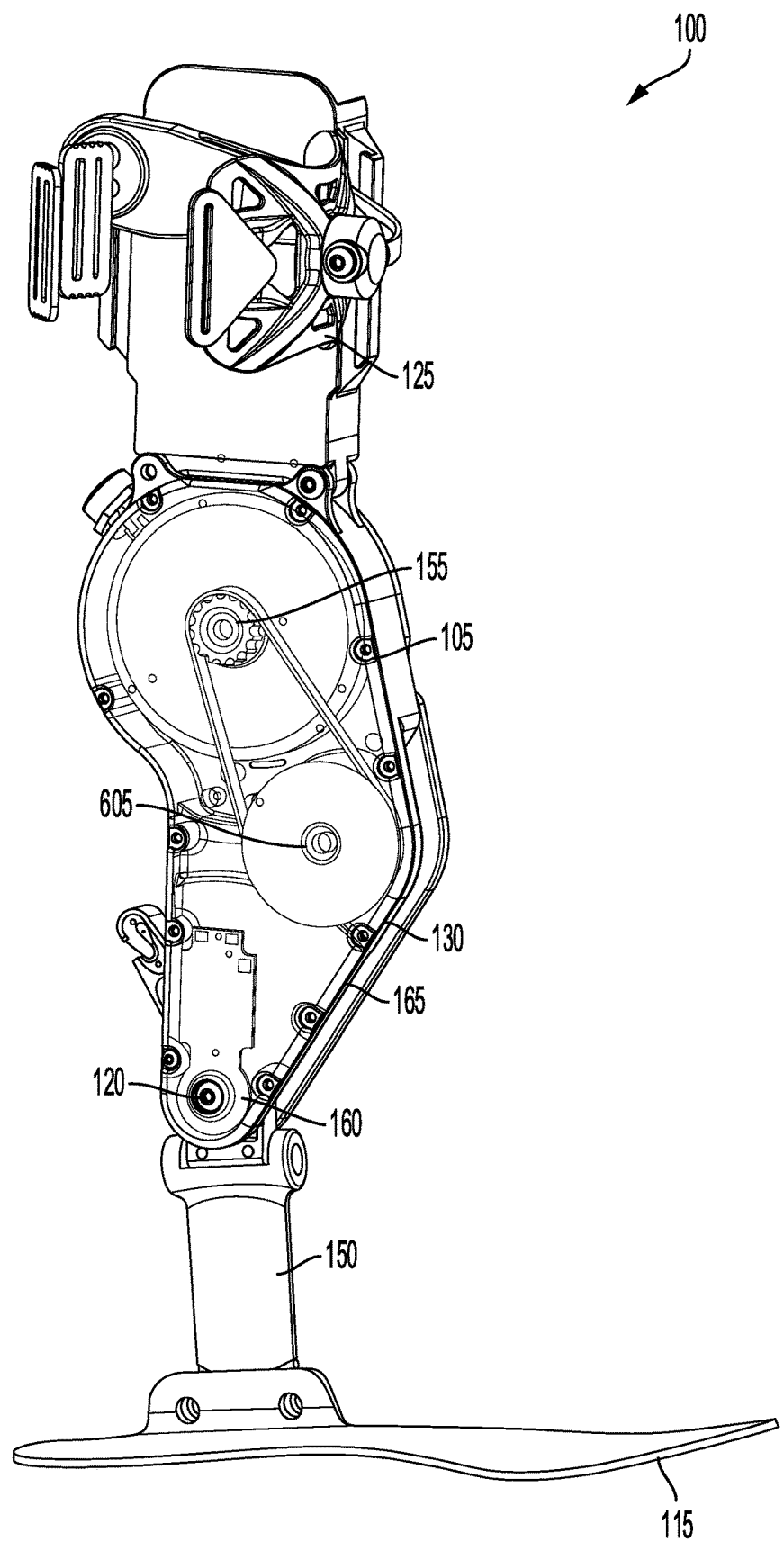
FIG. 8 illustrates a schematic diagram of an exoskeleton and internal parts, according to an embodiment.
Figure 9:
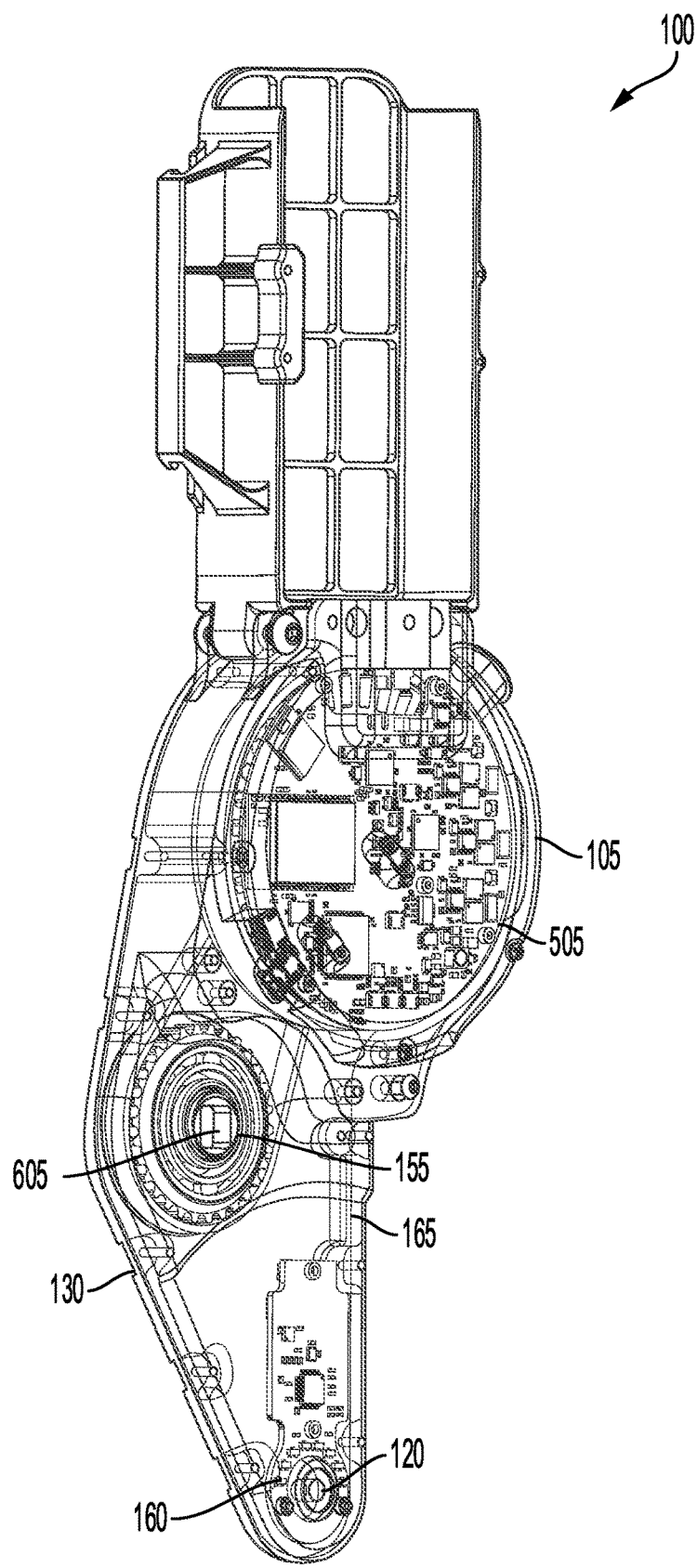
FIG. 9 illustrates a schematic diagram of an exoskeleton and internal parts, according to an embodiment.

FIG. 8 and FIG. 9 illustrate schematic diagrams of the exoskeleton 100 and internal parts. The exoskeleton 100 can include the one or more housings 105, the footplate 115, the ankle joint component 120, shin pad 125, the actuator 130, the post 150, the rotary encoder 155, the second rotary encoder 160, the sealant 165, and electronic circuitry 505 as described above. The internal parts can include an electronic circuit (e.g., circuitry). The electronic circuit can include individual electronic components (e.g., resistors, transistors, capacitors, inductors, diodes, processors, or controllers). The motor rotor can be connected to the output shaft 605.

Figure 10:
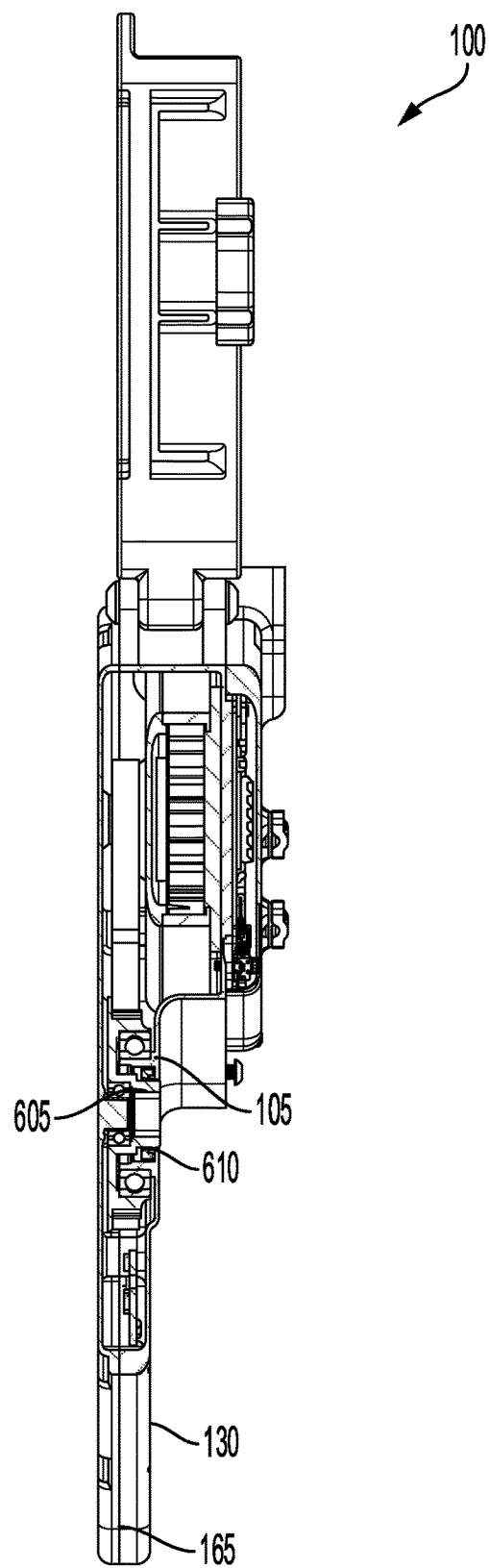
FIG. 10 illustrates a side view of an exoskeleton, according to an embodiment.

FIG. 10 illustrates a side view of the exoskeleton 100. The exoskeleton 100 can include the one or more housings 105, the actuator 130, the rotary encoder 155, the second rotary encoder 160, and the sealant 165, the output shaft 605, and the bore 610 as described above. The exoskeleton 100 can include an output shaft 605 (e.g., motor rotor). The output shaft 605 can be coupled to the electric motor. The output shaft 605 can extend through a bore 610 in a housing of the one or more housings 105 enclosing the electric motor. The bore 610 can receive the output shaft 605. A magnet can be located on a first side of the electric motor. An encoder chip can be located on the electronics board on the first side of the electric motor. The encoder chip can measure the angular position of the rotary encoder 155. An ankle shaft can extend through the second rotary encoder 160 which can increase the structural integrity of the exoskeleton 100. The exoskeleton 100 can include a transmission (e.g., gearbox) configured to couple the output shaft 605 to the electric motor. The transmission can include a machine in a power transmission system. The transmission can provide controlled application of power.

Figure 11:
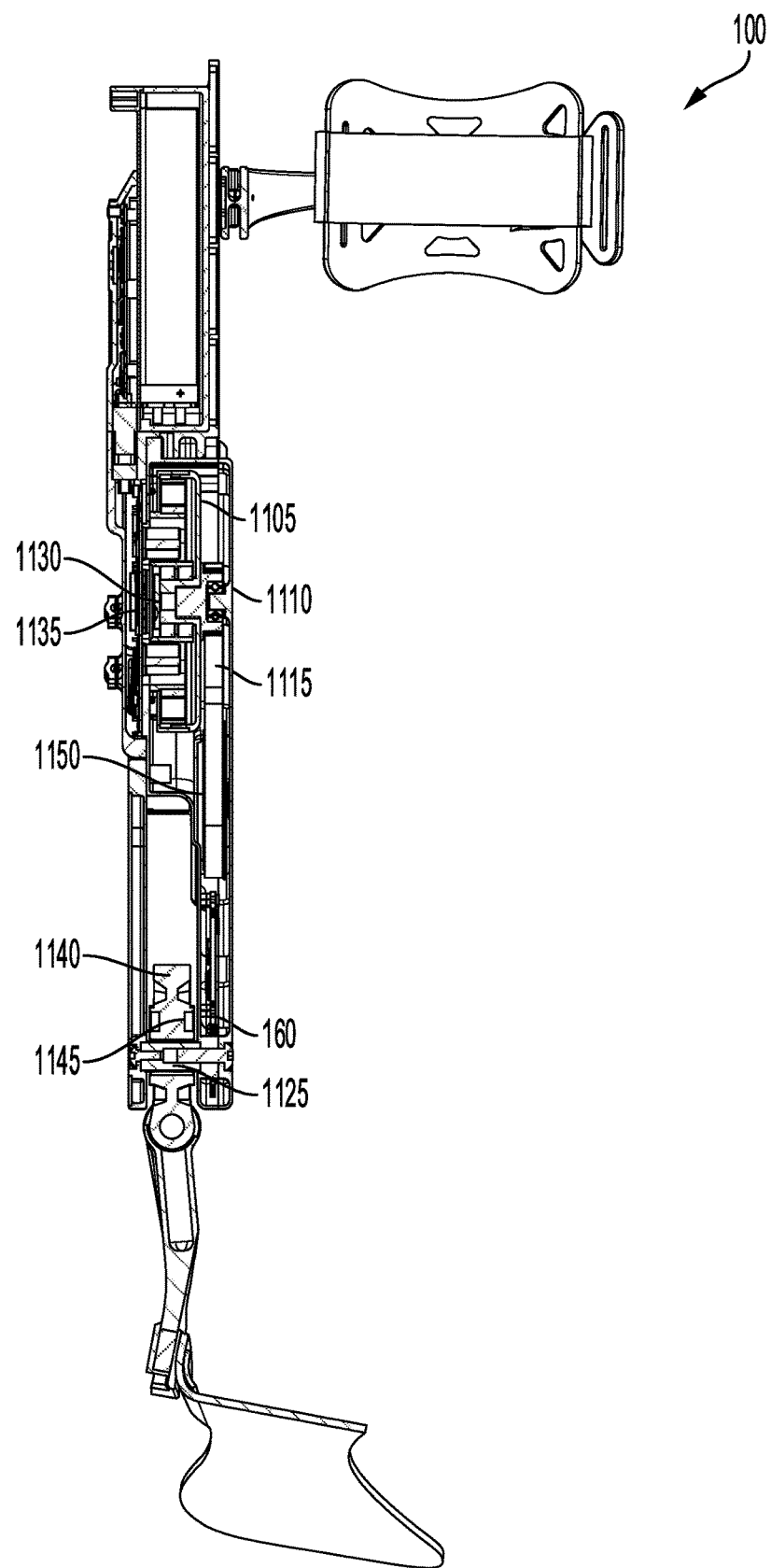
FIG. 11 illustrates a side view of an exoskeleton, according to an embodiment.

FIG. 11 illustrates a side view of an exoskeleton 100. The exoskeleton 100 can include a motor 1105 (e.g., electric motor), a motor timing pulley 1110 (e.g., timing pulley), a motor timing belt 1115 (e.g., timing belt), the second rotary encoder 160 (e.g., an ankle encoder PCB, ankle encoder printed circuit board, second rotary encoder PCB, or ankle encoder), an ankle shaft 1125, a motor encoder magnet 1130, a motor encoder 1135, a lever arm 1140 (e.g., ankle lever), and an ankle encoder magnet 1145. The ankle shaft 1125 can extend through the second rotary encoder 160 to increase the structural integrity of the exoskeleton 100. The motor timing belt 1115 can be coupled to a sprocket 1150. The sprocket 1150 can be coupled with a spool. The motor encoder magnet 1130 can be located on the first side of the electric motor.

Figure 12:
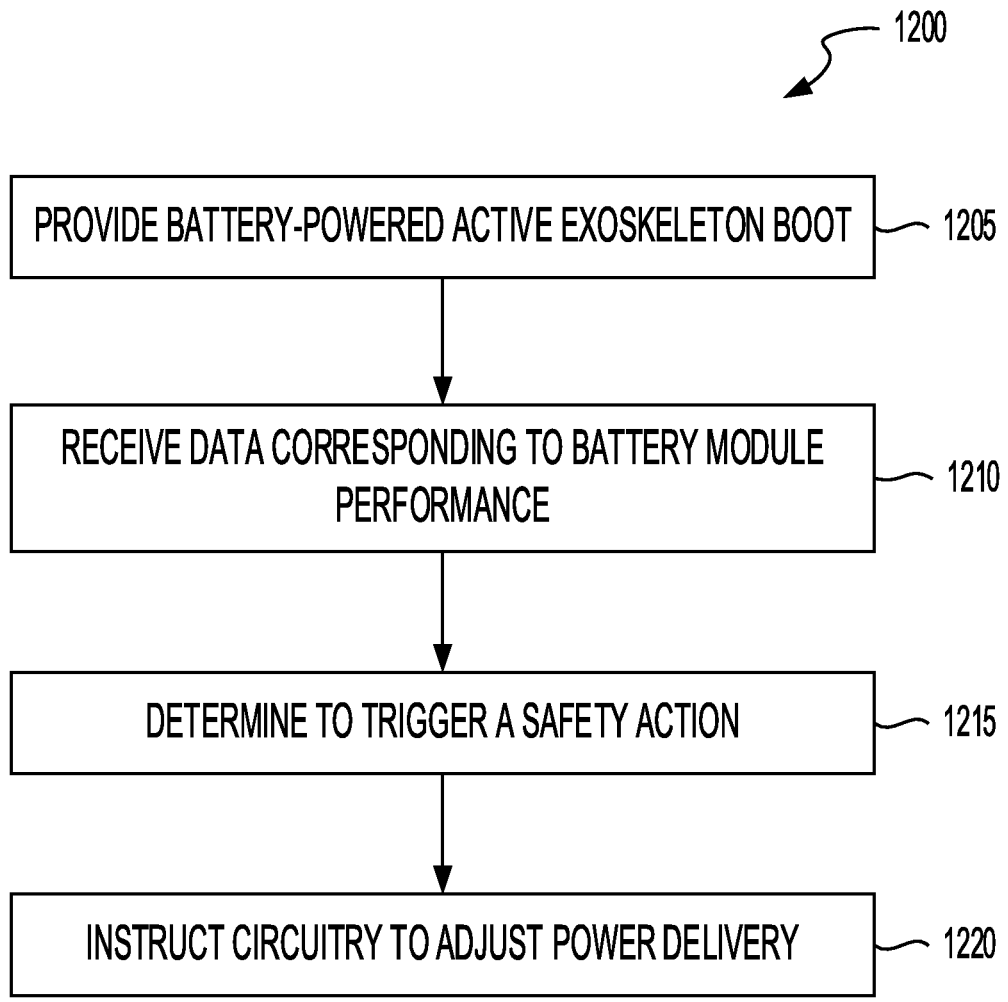
FIG. 12 illustrates a method of augmenting user motion, according to an embodiment.

FIG. 12 illustrates a method 1200 of augmenting user motion. The method 1200 can include providing, to a user, a battery-powered active exoskeleton boot (BLOCK 1205). The battery-powered active exoskeleton boot can include a shin pad to be coupled to a shin of a user below a knee of the user. The battery-powered active exoskeleton boot can include one or more housings enclosing electronic circuitry and an electric motor that can generate torque about an axis of rotation of an ankle joint of the user. At least one of the one or more housings can be coupled to the shin pad below the knee of the user. The battery-powered active exoskeleton boot can include a battery holder coupled to the shin pad. The battery holder can be located below the knee of the user and above the one or more housings enclosing the electronic circuitry. The battery-powered active exoskeleton boot can include a battery module removably affixed to the battery holder. The battery module can include a first power connector that electrically couples to a second power connector located in the battery holder while attached to the battery holder to provide electric power to the electronic circuitry and the electric motor. The battery-powered active exoskeleton boot can include an output shaft coupled to the electric motor and extending through a bore in a housing of the one or more housings enclosing the electric motor. The electronic circuitry can control delivery of power from the battery module to the electric motor to generate torque about the axis of rotation of the ankle joint of the user.

In some embodiments, the first power connector includes a blade connector. The second power connector can include a receptacle configured to receive the blade connector absent an exposed cable. The battery module can include a plurality of battery cells 305. The battery module can include a printed circuit board soldered to the plurality of battery cells 305. The battery module can include one or more battery balancers configured to actively transfer energy from a first battery cell 305 of the plurality of battery cells 305 to a second battery cell 305 of the plurality of battery cells 305 having less charge than the first battery cell 305. The battery module can include a signal trace, on the printed circuit board, that electrically connects the plurality of battery cells 305 to the one or more battery balancers.

In some embodiments, the method 1200 includes providing, via a serial data communication port of the first power connector, at least one of battery state data, a battery test function, a smart charging function, or a firmware upgrade. The battery state data can include the health of the battery module. The battery test function can include probing the battery module. The smart charging function can include using a high voltage to charge the battery module. A pin of the first power connector that provides serial data can be further configured to receive a voltage input greater than or equal to a threshold to wake up a battery management system of the battery module.

The method 1200 can include receiving data corresponding to battery module performance (BLOCK 1210). For example, the method 1200 can include receiving, by one or more processors of the battery-powered active exoskeleton boot, data corresponding to a performance of the battery module, the data comprising one or more of a temperature, current, voltage, battery percentage. For example, the data can include a temperature from one or more temperature sensors of the computing system. The data can include a temperature from one or more temperature sensors of the battery module.

The method 1200 can include determining to trigger a safety action (BLOCK 1215). For example, the method 1200 can include determining, by the one or more processors, based on a safety policy, to trigger a safety action. The safety policy can include triggering the safety action if a threshold temperature, voltage or battery percentage is crossed. For example, the safety policy can include triggering the safety action if a temperature of one or more of the plurality of battery cells 305 is higher than a threshold temperature. The safety policy can include triggering the safety action if a battery percentage of the battery module is below a threshold battery percentage. The measured temperature can include the temperature of the printed circuit board and battery cells 305. The measured temperature can include the temperature of the printed circuit board and battery cells 305 measured in two locations. The safety policy can include triggering the safety action if a measured voltage is higher than the threshold voltage.

The method 1200 can include instructing circuitry to adjust power delivery (BLOCK 1220). For example, the method 1200 can include instructing, by the one or more processors, based on the safety action, the electronic circuitry to adjust delivery of power from the battery module to the electric motor to reduce an amount of torque generated about the axis of rotation of the ankle joint of the user. The safety action can include lowering or reducing the amount of torque generated about the axis of rotation of the ankle joint of the user. The safety action can include increasing the amount of torque generated about the axis of rotation of the ankle joint of the user.

Figure 13:
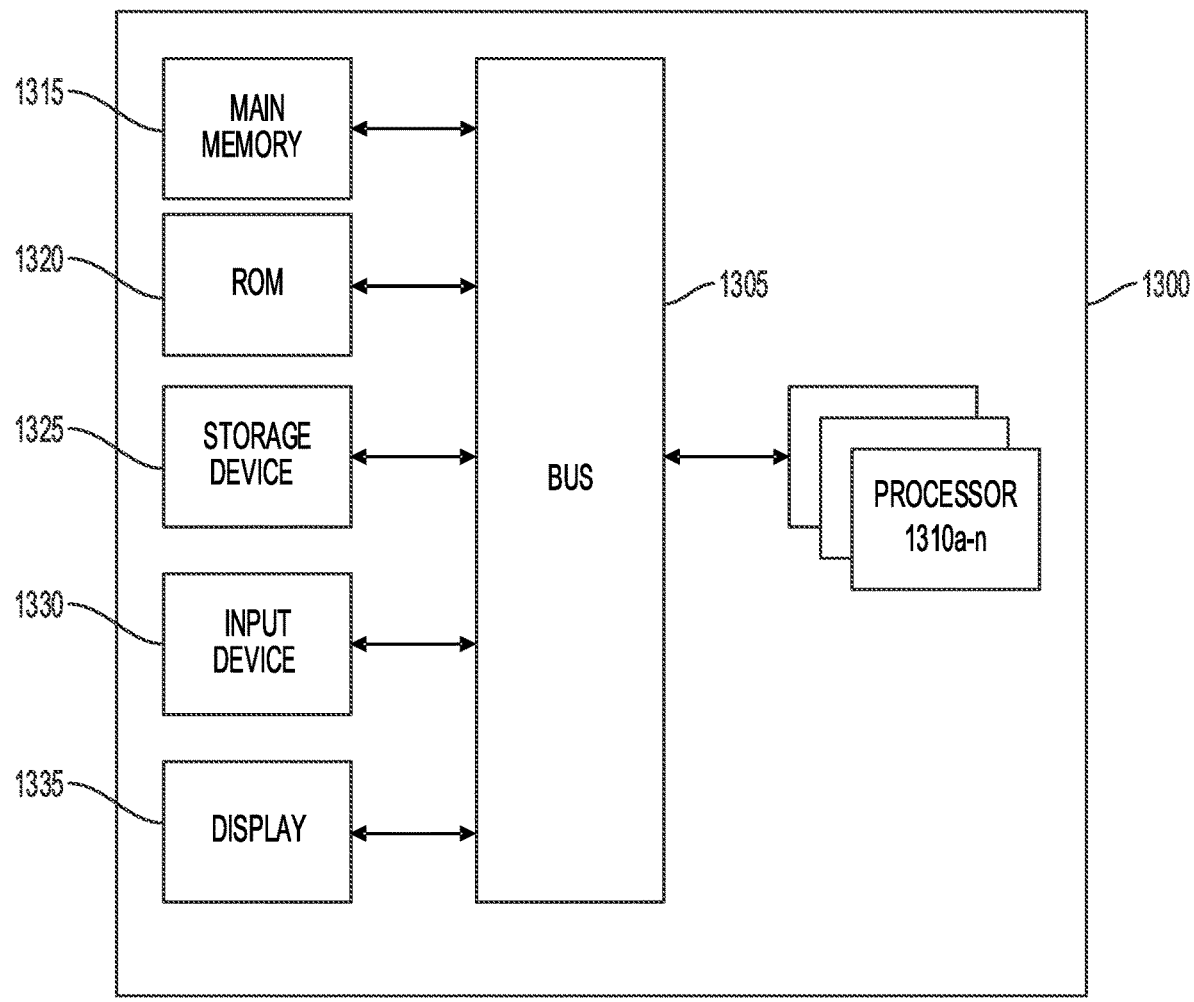
FIG. 13 illustrates a block diagram of an architecture for a computing system employed to implement various elements of the system and methods depicted in FIGS. 1-21, according to an embodiment.

FIG. 13 illustrates a block diagram of an architecture for a computing system employed to implement various elements of the system and methods depicted in FIGS. 1-21, according to an embodiment. FIG. 13 is a block diagram of a data processing system including a computer system 1300 in accordance with an embodiment. The computer system can include or execute a coherency filter component. The data processing system, computer system or computing device 1300 can be used to implement one or more components configured to process data or signals depicted in FIGS. 1-12 and 14-16. The computing system 1300 includes a bus 1305 or other communication component for communicating information and a processor 1310a-n or processing circuit coupled to the bus 1305 for processing information. The computing system 1300 can also include one or more processors 1310 or processing circuits coupled to the bus for processing information. The computing system 1300 also includes main memory 1315, such as a random access memory (RAM) or other dynamic storage device, coupled to the bus 1305 for storing information, and instructions to be executed by the processor 1310. Main memory 1315 can also be used for storing time gating function data, temporal windows, images, reports, executable code, temporary variables, or other intermediate information during execution of instructions by the processor 1310. The computing system 1300 may further include a read only memory (ROM) 1320 or other static storage device coupled to the bus 1305 for storing static information and instructions for the processor 1310. A storage device 1325, such as a solid state device, magnetic disk or optical disk, is coupled to the bus 1305 for persistently storing information and instructions.

The computing system 1300 may be coupled via the bus 1305 to a display 1335 or display device, such as a liquid crystal display, or active matrix display, for displaying information to a user. An input device 1330, such as a keyboard including alphanumeric and other keys, may be coupled to the bus 1305 for communicating information and command selections to the processor 1310. The input device 1330 can include a touch screen display 1335. The input device 1330 can also include a cursor control, such as a mouse, a trackball, or cursor direction keys, for communicating direction information and command selections to the processor 1310 and for controlling cursor movement on the display 1335.

The processes, systems and methods described herein can be implemented by the computing system 1300 in response to the processor 1310 executing an arrangement of instructions contained in main memory 1315. Such instructions can be read into main memory 1315 from another computer-readable medium, such as the storage device 1325. Execution of the arrangement of instructions contained in main memory 1315 causes the computing system 1300 to perform the illustrative processes described herein. One or more processors in a multi-processing arrangement may also be employed to execute the instructions contained in main memory 1315. In some embodiments, hard-wired circuitry may be used in place of or in combination with software instructions to effect illustrative implementations. Thus, embodiments are not limited to any specific combination of hardware circuitry and software.

Although an example computing system has been described in FIG. 13, embodiments of the subject matter and the functional operations described in this specification can be implemented in other types of digital electronic circuitry, or in computer software, firmware, or hardware, including the structures disclosed in this specification and their structural equivalents, or in combinations of one or more of them.

III. Controller for Exoskeleton

A controller can be provided to generate commands for an exoskeleton to control the operation of the exoskeleton, for example, in real-time as a user is performing one or more activities based in part on real-time data (e.g., sensor data) associated with the user performing the one or more activities to augment and aid the user through the exoskeleton in performing the activities. The controller can update or modify commands indicating torque to be applied to a limb of the user through the exoskeleton based in part on feedback as the user is performing the activities. In embodiments, the controller can generate commands to correct or provide a desired level of torque or force through the exoskeleton to aid the user in performing the activities at the correct or appropriate time, for example, using the real-time feedback.

A controller can be designed for a predetermined steady state gait for a person (e.g., subject A walking at 3 mph on a treadmill). A software engineer can collect data and then use heuristics to produce a target torque profile for controlling operation of an exoskeleton based on the collected data. Exoskeleton controllers may be difficult to design based on a variety of factors, including subtle or significant differences between different users' ambulation profiles, the application of torque or force affects different users' gait in unknown ways, the number of conditions the controller may need to account for, the control of transitions between different states, the lack of a single cost-function that can be optimized in real-time, and the lack of a clarity of what sensors should be used to predict the target torque. Conditions that the controller may need to account for can include different types of people (e.g., age, size, ability, etc.), different types of gait (e.g., walking, running, jumping, etc.), different terrains (e.g., pavement, grass, sand, ice, etc.), different speeds (e.g., slow, medium, fast, etc.), different target power levels (e.g., high augmentation, transparent, low, etc.). The transition between different states can have O(2) occurrences. If the controller supports N discrete steady state behaviors, then there can be approximately $N^2$ possible transitions.

Exoskeleton controllers as described herein can convert real-time sensor data into motor commands. Exoskeleton controllers can be broken into three levels: high level, mid-level, and low level. High level controllers can include activity recognition (e.g., walking, running, sitting, etc.). Mid-level controllers can include development of a torque profile based on recognized activity (e.g., converting activity into torque). Low level controllers can include execution of the mid-level torque profile (e.g., motor commands, field oriented control of brushless DC motors, current causing torque or speed, etc.). Functions can be developed that first recognize an activity and then use additional algorithms that develop torque profiles. However, various factors including those enumerated above can make it technically difficult or challenging to determine the torque profile for a particular activity is. Functions including a high level, mid-level, and low level controller can be termed 3L controllers because the algorithm has 3 levels. Functions including a high level and low level controller can be termed 2L controllers because the algorithm has 2 levels. The function can convert sensor data into motor commands. For example, the function can determine the torque and then execute (e.g., apply) the torque.

3L controllers can be developed by engineers for specific actions. The testing environment can be controlled to known conditions where the controller behaves correctly. Data can be collected while using the 3L controllers. Machine learning can be used to predict 3L controller torques during these conditions. The machine learning controllers may have interpolation and extrapolation capabilities that go beyond the capabilities of the 3L controllers. The machine learning controller may correctly predict the required torque between states that the 3L controller does not control for. The machine learning controller may reduce the number of 3L controllers that need to be written by engineers. The machine learning controller may learn how to interpolate and extrapolate the controller to untrained movements, including gait transitions. This may reduce the number of hand-written controllers and make transitions between states more seamless. However, engineers may still need to create the 3L controllers to train the machine learning engine. These controllers may be practically difficult and time consuming to create (e.g., one controller can take months to develop) so that they generalize across people. For example, even if one knows a user will be walking upstairs, it may be difficult to write a controller that applies the correct torque when anyone goes up the stairs. The bulk of a control developer's work can be in developing the algorithms to create a target torque profile given a certain gait. Machine learning can occur from heuristic torque controllers. The sensor input may not change if the machine learning torque command is identical.

Systems and methods in accordance with this technical solution can receive sensor data from one or more sensors monitoring a user, such as a user in motion. The sensor data can include data from position sensors of a motion capture system (e.g., accelerometers, gyroscopes) coupled with the user, as well as image data (e.g., video data) from one or more image capture devices (e.g., cameras, including three-dimensional cameras). The sensor data from multiple sensors can be correlated based on timestamps at which the sensor data is detected. The sensor data or a representation thereof can be presented to an operator, such as an expert, using a user interface (e.g., a display that presents the sensor data). An indication of a torque profile can be received from the user interface, such as responsive to the operator drawing the torque profile on the representation of the sensor data. The torque profile can include an indication of torque at a plurality of points in time corresponding with the sensor data. The torque profile can include an indication of relationships between parameters such as torque, time, and angle. A machine learning model can be trained using training data that includes sensor data as input and torque profiles as output. For example, the sensor data can be provided as input to the machine learning model, which can be caused to generate a candidate output. The candidate output can be compared with the torque profile, and the machine learning model can be modified responsive to the comparison, such as by using an optimization algorithm to reduce or minimize a difference between the candidate output and the torque profile, such as by adjusting various weights or biases associated with components of the machine learning model. As such, the machine learning model can be trained to determine torque profiles using sensor data without requiring complex, predetermined heuristics to be applied to first detect the activity, then determine the torque profile based on the activity.

In some embodiments, users perform various activities (e.g., steady state, transient, etc.), while wearing a collection of sensors. The users can be videotaped or part of a motion capture system. An expert can replay the data (e.g., using video) and generate the correct (e.g., ground truth) torque profiles post-hoc. This could be done with a visualization software that allows the expert to step through the trial and simultaneously see the required data. The expert can "draw" the torque profiles to what the expert believes is optimal. The activities may or may not be tagged. The expert can add context to the transitions. Machine learning can be used to learn these torque profiles with the constraint of only using real-time sensor data (e.g., without using future data). Users can wear the devices using the machine learning models and real-time optimization is used to alter the commands to reach the target torque profiles. Users may have the ability to alter their own profiles in real-time, further informing the models. The machine learning engine can determine the level of torque that should be applied to the exoskeleton at any given point in time.

In some embodiments, there is an additional step after the expert draws a few torque profiles. Machine learning techniques as described herein can be used to replace the expert. For example, an expert can produce the torque profile for 100 different steps. Machine learning can be used in an unconstrained manner to learn the expert's techniques with access to all the data (e.g., past data, future data, etc.) including the device data and any extra sensors (e.g., motion capture, video, force plates, etc.). In this way, the machine learning engine can generate much more training data much faster for the real-time machine learning model that is being used on the device.

Benefits of the aforementioned embodiments can include the following. The control developer may not need to create 3L controllers. It can be much easier and faster to create post-hoc torque profiles. The expert or control developer can use their understanding of biomechanics and their access to unconstrained data to generate torque profiles quickly. The expert can see transitions and determine how the transitions should be managed. The transitions do not need to be anticipated for the transitions are simply observed.

An expert can initially label data that is collected during unpowered use of an exoskeleton. Once the expert's torque profiles are used to develop a controller, a user can try to use this controller. The application of torque can affect the sensor readings. For example, compliance in the system will affect the ankle angle measurement. If the biological ankle is held at 90 degrees, the ankle angle sensor may read 90 degrees when unpowered, but once torque is applied, it may read something different. The issue can be that for a given gait, the sensor readings can be different than what the expert was using. This may not affect the expert's ability to repeat the labeling process, but it may affect the machine learning model.

In some embodiments, iterative training cycles (e.g., cycle 1, cycle 2, cycle 3, cycle 4, etc.) can be used to converge. Cycle 1 can include unpowered data. Cycle 2 can include imperfect powered data. Cycle 3 can include improved powered data. Additional cycles can include improved powered data over the previous cycle. An iterative approach can be used during the gathering of sensor data.

In some embodiments, characterization and system identification (ID) techniques can be used to predict how the application of torque will affect the sensor readings. System ID can be done to map exoskeleton torque to sensor changes, or artificial intelligence (AI) can be used to create this map. The AI can use this to model the "unpowered" sensor readings when torque is being applied. For example, the machine learning engine can learn a torque trajectory based on unpowered sensor data (e.g., from an expert or machine learning engine trained by expert). The machine learning engine can begin to apply torque. The machine learning engine can use a characterization model to convert sensors reading under load to unpowered sensor readings. The machine learning engine can use the simulated unpowered sensor reading to calculate appropriate torque.

In some embodiments, a 2L controller can be done without AI. In some embodiments, experts could also tag basic features (e.g., toe-off, heel strike, etc.) to fine tune the lower level algorithms. In some embodiments, an expert can list what transitions are possible or likely. For example, if a user is running, the chances that the user is sitting in the next step are low. In some embodiments, the machine learning engine could be learning the parameters to a physiological model instead of a wide open space. Forcing the machine learning engine to generate an unconstrained torque profile may be impractical. The machine learning engine can fit within a model (e.g., an impedance controller that can only update at a low frequency). The model can be physiologically inspired, like a muscle model. The machine learning engine can fit the model parameters and not generate the entire torque profile. In some embodiments, constraints can be placed on the system. An example constraint can include preventing the machine learning engine from switching the torque from 0 (or no torque) to maximum torque instantaneously (e.g., within a predetermined amount of time such).

Figure 14:
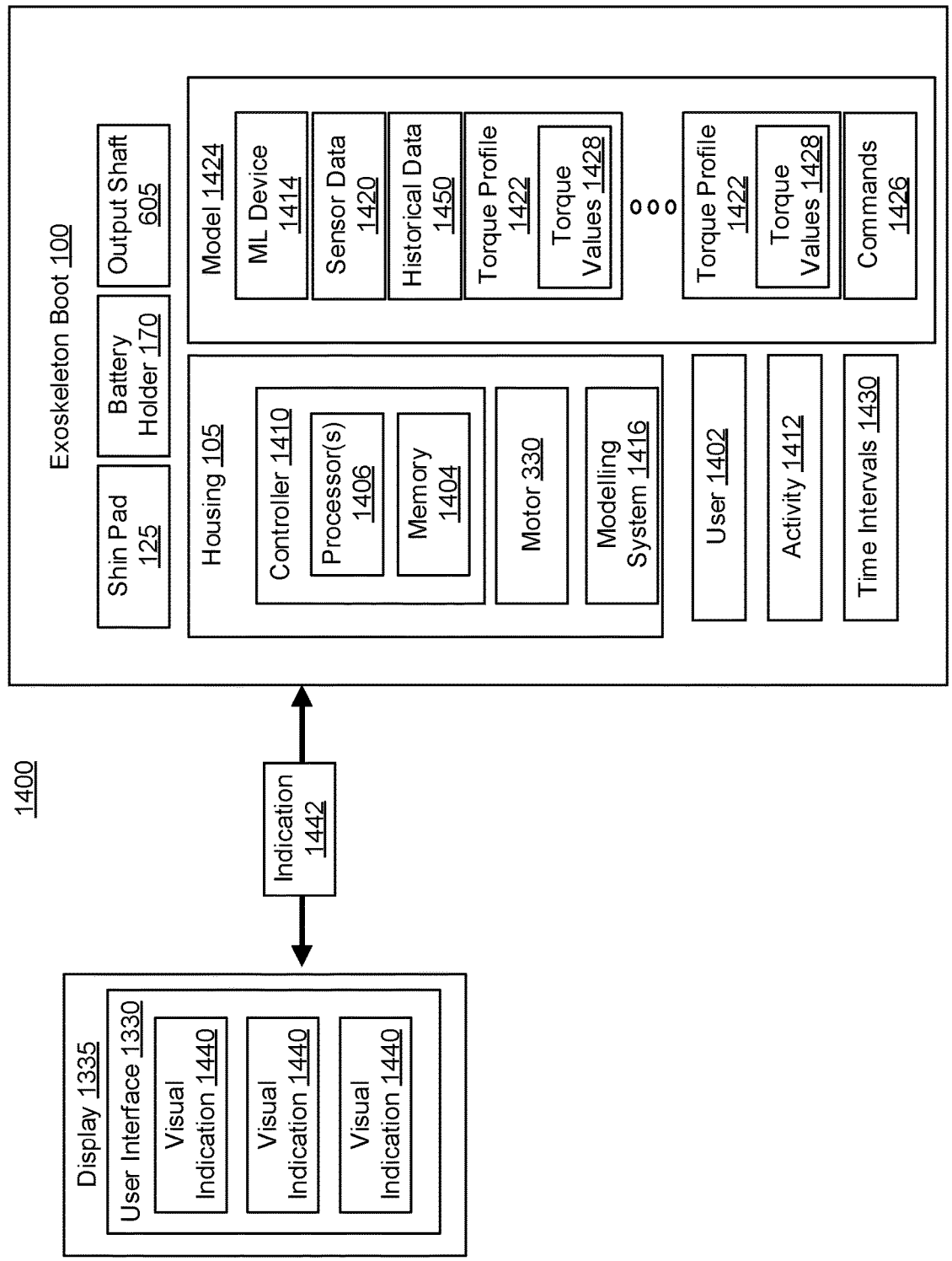
FIG. 14 is a block diagram of a system for augmenting motion via a battery-powered active exoskeleton boot in accordance with an illustrative embodiment.

Referring to FIG. 14, depicted is a block diagram of one embodiment of a system 1400 having an exoskeleton boot 100 for augmenting motion of a user 1402 during one or more activities 1412. The exoskeleton boot 100 can be the same as or substantially similar to exoskeleton 100 described herein with respect to FIG. 1 or any type of exoskeleton described herein. The exoskeleton boot 100 can include one or more components to couple with a lower limb of the user 1402. For example, the exoskeleton boot 100 can include a shin pad 125 to couple to a shin of the user 1402 below a knee of the user 1402. The exoskeleton boot 100 can include one or more housings 105. At least one of the housings 105 can couple to the shin pad 125 below the knee of the user 1402. The housings 105 can enclose or include a controller 1410 having a memory 1404 and one or more processors 1406, for example, coupled to the memory 1404. The housings 105 can enclose or include, but not limited to, an electric motor 330 that generates to torque about an axis of rotation of an ankle joint of the user 1402. The housings 105 can provide protection for the controller 1410 and electronic motor 330 from various environmental elements or conditions (e.g., water, rain, snow, mud, dirt) of an environment the exoskeleton boot 100 is being used or worn. The housing 105 can be formed to cover or encapsulate the electronic circuitry, sensors and/or motors, including the controller 1410 and electronic motor 330.

The exoskeleton boot 100 can include a battery holder 170 coupled to the shin pad 125. The battery holder 170 can include or correspond to a cavity, compartment, chamber or structure shaped and designed to hold a battery module 145, for example, in place during operation or use of the exoskeleton boot 100. The exoskeleton boot 100 can include an output shaft 605 coupled to the electric motor 330. For example, the output shaft 605 can extend through a bore 610 in a housing 105 of the one or more housings 105 enclosing the electric motor 330 to couple to the electric motor 330. The shin pad 125, housing 105, battery holder 170, output shaft 605 can be the same as or substantially similar to shin pad 125, housing 105, battery holder 170 described herein with respect to FIG. 1 and the output shaft 605 described above with respect to FIG. 6. or any type of exoskeleton described herein.

The exoskeleton boot 100 an include a controller 1410. The controller 1410 can be implemented using hardware or a combination of software and hardware. For example, each component of the controller 1410 can include logical circuitry (e.g., a central processing unit or CPU) that responses to and processes instructions fetched from a memory unit (e.g., memory 1404). Each component of the controller 1410 can include or use a microprocessor or a multi-core processor. A multi-core processor can include two or more processing units (e.g., processor 1406) on a single computing component. Each component of the controller 1410 can be based on any of these processors, or any other processor capable of operating as described herein. Each processor can utilize instruction level parallelism, thread level parallelism, different levels of cache, etc. For example, the controller 1410 can include at least one logic device such as a computing device having at least one processor 1406 to communicate, for example, with a user device, display device 1335 and one or more exoskeleton boots 100. The components and elements of the controller 1410 can be separate components or a single component. The controller 1410 can include a memory component (e.g., memory 1404) to store and retrieve sensor data 1420. The memory 1404 can include a random access memory (RAM) or other dynamic storage device, for storing information, and instructions to be executed by the controller 1410 and command modelling system 1416. The memory 1404 can include at least one read only memory (ROM) or other static storage device for storing static information and instructions for the controller 1410. The memory 1404 can include a solid state device, magnetic disk or optical disk, to persistently store information and instructions. The controller 1410 can be the same as or substantially similar to any controller or microcontroller described herein.

The controller 1410 can include or connect with a command modelling system 1416. The command modelling system 1416 can include, generate and/or execute a model 1424 to generate commands 1426. The command modelling system 1416 can be implemented using hardware or a combination of software and hardware. The command modelling system 1416 can include logical circuitry (e.g., a central processing unit or CPU) that responses to and processes instructions fetched from memory 1404. The command modelling system 1416 can include a processor and/or communicate with processor 1406 to receive instructions and execute instructions (e.g., train model 1424) received, for example, from controller 1410.

The model 1424 can include or execute a machine learning device 1414 (e.g., machine learning engine) having one or more machine learning algorithms. In embodiments, the model 1424 can be trained to predict torque values 1428 and torque profiles 1422 and generate one or more commands 1426 corresponding to the torque values 1428 and torque profiles 1422. The machine learning device 1414 can identify patterns or similarities between different data points of the received input (e.g., sensor data 1420) and map the inputs to outputs that correspond to the identified patterns (e.g., ankle angle data, torque used to transition between walking and running in previous activities). The model 1424 can generate the commands 1426 based in part on the identified patterns in the received input data. The machine learning device 1414 can be implemented using hardware or a combination of software and hardware. In embodiments, the machine learning device 1414 can include circuitry configured to execute one or more machine learning algorithms.

The exoskeleton boot 100 can couple with or connect to (e.g., wireless connection) to a display 1335 (e.g., display device). The display 1335 can provide, for example, information to the user 1402 including but not limited to, torque profiles 1422, historical video data 1450, historical motion capture data 1450 and/or data associated with a user 1402 performing one or more activities 1412 wearing the exoskeleton boot 100. The display 1335 can provide or display one or more visual indications 1440. The visual indication 1440 can include a video of the user 1402 performing an activity 1412, an image of the user 1402 performing an activity 1412, a marker, menu, window or selectable content item provided through the display 1335. The visual indication 1440 can include a menu or listing of torque profiles 1422 available for selection through the display 1335 or user interface 1330 portion of the display 1335 (e.g., touch screen, selectable content items). The display 1335 can be the same as or substantially similar to the display 1335 described above with respect to FIG. 13.

In embodiments, a user interface 1330 (e.g., input device) can couple with or connect to the display 1335 to, for example, enable a user 1402 to interact with content provided through the display 1335. The user interface 1330 can include enable interaction with one or more visual indications 1440 provided through the display 1335 and responsive to an interaction (e.g., select, click-on, touch, hover), the user interface 1330 can generate an indication 1442 identifying a user input and/or selection of at least one content item (e.g., visual indication 1440). The user interface 1330 can couple to or connect with the exoskeleton boot 100 to provide the indication 1442. In some embodiments, the display 1335 can receive the indication 1442 from the user interface 1330 and transmit or provide the indication 1442 to the exoskeleton boot 100. The user interface 1330 can be the same as or substantially similar to the input device 1330 described above with respect to FIG. 13.

The controller 1410 can store and maintain data, including sensor data 1420, based in part on time intervals 1430 corresponding to a time period when one or more activities 1412 were performed. Time intervals 1430 can include or correspond to a time period or range of time having an initial time and an end time. The number of time intervals 1430 can vary (e.g., first time interval 1430, second time interval 1430) and be based at least in part on a number of activities 1412 tracked, a number of users 1402, and/or an amount of sensor data 1420.

The sensor data 1420 can include, but is not limited to, motion data, force data, torque data, temperature data, speed, gait transitions, angle measurements (e.g., of different joints of the user 1402). The sensor data 1420 can include data corresponding to steady state activities 1412 or transient activities 1412. The sensor data 1420 can include any form of data associated with, corresponding to or generated in response one or more activities 1412 performed or executed by the user 1402 wearing the exoskeleton boot 100. For example, the sensor data 1420 can include data associated with a movement or motion performed or executed by the user 1402 and/or any type of use of one or more muscles of the user 1402, for example, that may not involve motion (e.g., holding a position, standing) while wearing the exoskeleton boot 100. The sensor data 1420 can include ankle joint data, inertial measurement unit data, and/or battery data.

In embodiments, the sensor data 1420 can include historical data 1450. The historical data 1450 can include historical sensor data 1450, historical video data 1450 and historical motion capture data 1450. The historical sensor data 1450 can include previous sensor data 1420 associated with the user 1402 performing one or more activities 1412 or sensor data 1420 from one or more other, different users 1402 performing one or more activities 1412. The historical video data 1450 can include one or more videos, images or stream of images of the user 1402 and/or one or more other, different users 1402 performing one or more activities 1412. The historical motion capture data 1450 can include one or more recordings or images of the user 1402 and/or one or more other, different users 1402 performing one or more activities 1412.

The historical motion capture data 1450 can include or correspond to data collected via the exoskeleton boot 100 in a plurality of states, for example, an unpowered state, a partially powered state, and a fully powered state. The historical motion capture data 1450 can include inertial measurement unit data, goniometer data, infrared reflector data, force plate data, electromyography (EMG) data, and heartrate data. The historical data 1450 can be received from a plurality of different systems (e.g., plurality of sensors, plurality of exoskeleton boots, plurality of user devices, plurality of controllers) and the controller 1410 can perform one or more of the following, averaging, filtering, aggregating and/or merging to process the historical data 1450 and provide to the model 1424. For example, the controller 1410 can average the historical data 1450 to identify patterns, trends or similarities across different data points. The controller 1410 can filter the historical data 1450 to identify patterns, trends or similarities across different data points. The controller 1410 can aggregate or merge the historical data 1450 to identify patterns, trends or similarities across different data points. In embodiments, the controller 1410 can generate a data set using the historical data 1450 to provide to the model 1424 for training the model 1424.

The commands 1426 can include an instruction, task or function generated by the model 1424 and provided to an exoskeleton boot 100 to instruct the exoskeleton boot 100 a level or amount of torque, force, velocity or a combination of torque, force and velocity (e.g., impedance) to generate to aid a user wearing the respective exoskeleton boot 100 in performing an activity 1412. In embodiments, the commands 1426 can include a data structure indicating a desired, requested or target torque, force and/or velocity level. The commands 1426 can include or correspond to a torque profile 1422 that includes one or more torque values 1428 (e.g., or force values, velocity values) for the exoskeleton boot 100 to apply to a lower limb of the user 1402 to augment or aid the user 1402 in performing an activity 1412.

Figure 15:
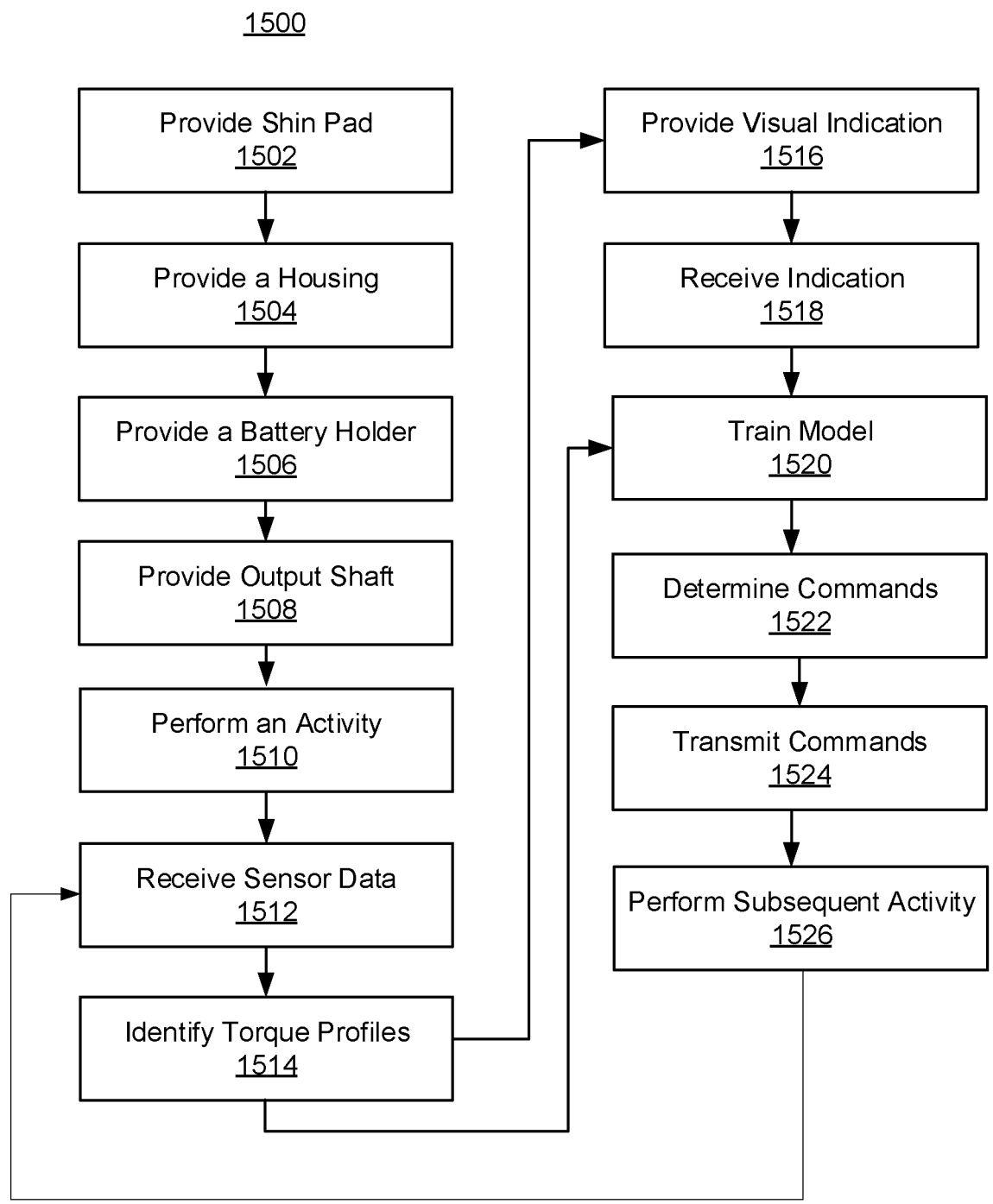
FIG. 15 illustrates a method of augmenting motion via a battery-powered active exoskeleton boot, according to an embodiment.

Referring now to FIG. 15, depicted is a flow diagram of one embodiment of a method 1500 for method of augmenting motion via a battery-powered active exoskeleton boot in accordance with an illustrative embodiment. In brief overview, the method 1500 can include one or more of: providing a shin pad of an exoskeleton boot (1502), providing a housing (1504), providing a battery holder (1506), providing an output shaft (1508), performing an activity (1510), receiving sensor data (1512), identifying one or more torque profiles (1514), providing a visual indication (1516), receiving an indication (1518), training the model (1520), determining one or more commands (1522), transmitting one or more commands (1524), and performing a subsequent activity (1526). The functionalities of the method 1500 may be implemented using, or performed by, the components detailed herein in connection with FIGS. 1-14 and 16.

Referring now to operation (1502), and in some embodiments, a shin pad 125 can be provided, for example, of an exoskeleton boot 100 for coupling to a shin of a user 1402 below a knee of the user 1402. The shin pad 125 can be a component or portion of the exoskeleton boot 100. The shin pad 125 can be coupled to (e.g., connected to, attached to, directly connected to) to the exoskeleton boot 100. The shin pad 125 can couple with or contract the shin of the user 1402, for example, to aid in connecting or securing the exoskeleton boot 100 to a lower limb of the user 1402. The shin pad 125 can be positioned, when the user 1402 is wearing the exoskeleton boot 100, to provide support and/or comfort to the respective lower limb that the exoskeleton boot 100 is coupled.

Referring now to operation (1504), and in some embodiments, one or more housings 105 can be provided. The exoskeleton boot 100 can include one or more housings 105 to hold, enclose or contain, but not limited to, electronic circuitry, sensors and/or motors of the exoskeleton boot 100. For example, the housings 105 can enclose or include a controller 1410 having a memory 1404 and one or more processors 1406, for example, coupled to the memory 1404. The housings 105 can enclose or include, but not limited to, an electric motor 330 that generates to torque about an axis of rotation of an ankle joint of the user 1402. The housings 105 can provide protection for the controller 1410 and electronic motor 330 from various environmental elements or conditions (e.g., water, rain, snow, mud, dirt) of an environment the exoskeleton boot 100 is being used or worn. The housing 105 can be formed to cover or encapsulate the electronic circuitry, sensors and/or motors, including the controller 1410 and electronic motor 330. The positioning of the housings 105 on the exoskeleton boot 110 can vary, based at least in part on a type of exoskeleton 100 and one or more other components (e.g., shin pad 125, encoders 155, 160) of the exoskeleton 100. In embodiments, at least one of the one or more housings 105 can be coupled to (e.g., connected to) the shin pad 125 below the knee of the user 1402.

Referring now to operation (1506), and in some embodiments, a battery holder 170 can be provided, for example, coupled to the shin pad 125. The battery holder 170 can be configured to receive, connect to or hold a battery module 145. The battery holder 170 can include or correspond to a cavity, compartment, chamber or structure shaped and designed to hold the battery module 145, for example, in place during operation or use of the exoskeleton boot 100. In embodiments, the battery holder 170 can secure or hold the battery module 145 motionless (or limit movement of battery module 145) during operation or use of the exoskeleton boot 100. In some embodiments, the battery holder 170 can enclose the battery module 145 and include material to provide protection for the battery module 145 from various environmental elements or conditions of an environment the exoskeleton boot 100 is being used or worn. The positioning of the battery holder 170 on the exoskeleton boot 110 can vary, based at least in part on a type of exoskeleton 100 and one or more other components (e.g., shin pad 125, encoders 155, 160) of the exoskeleton 100. In embodiments, the battery holder 170 can couple with or connect to the shin pad 125 of the exoskeleton boot 100 and below the knee of the user 1402.

Referring now to operation (1508), and in some embodiments, an output shaft 605 can be provided, for example, coupled to the electric motor 330 and extending through a bore 610 in a housing 105 of the one or more housings 105 enclosing the electric motor 330. The output shaft 605 can connect to (e.g., directly connect to) the electric motor 330. In embodiments, the output shaft 605 can extend through a bore 610 in a housing 105 of the one or more housings 105 enclosing the electric motor 330 to couple with the electric motor 330.

Referring now to operation (1510), and in some embodiments, an activity 1412 can be performed using the exoskeleton boot 100. The exoskeleton boot 100 can augment or aid the user 1402 in performing one or more activities 1412. In embodiments, the exoskeleton boot 100 can provide force, torque and/or power to the lower limb of the user 1402 the exoskeleton boot 100 is coupled to with to augment the movement of the user 1402 during the activity 1412. The activity 1412 can include steady state activities or transient activities. The activity 1412 can vary and can include any type of movement or motion performed or executed by the user 1402 and/or any type of use of one or more muscles of the user 1402, for example, that may not involve motion (e.g., holding a position, standing). For example, the activity 1412 (e.g., physical activity 1412) can include, but is not limited to, walking, running, standing, standing up, ascend or descend a surface (e.g., stairs), jogging, springing, jumping (e.g., single leg or both legs) squat, crouch, kneel or kick. In embodiments, the exoskeleton boot 100 can transfer energy to the lower limb of the user 1402 to augment the movement of the user 1402 during the activity 1412. The exoskeleton boot 100 can reduce a difficulty of performing the respective activity 1412 or multiple activities 1412 by reducing the energy or effort the user 1402 exerts to perform the respective activity 1412.

In some embodiments, the activities 1412 can include an initial activity 1412 or test activity 1412 performed under determined or specific conditions to generate and obtain sensor data 1420. For example, the activities 1412 an include specific actions (e.g., walk, run, jump) to test a performance of the user 1402 using the exoskeleton boot 100 and generate initial or baseline sensor data 1420. The activities 1412 can be performed in specific conditions or under test conditions, such as but not limited to, indoors, outdoors, or jumping to specific heights, where the conditions are known and can be factored with or aggregated with the associated sensor data 1420 to generate baseline sensor data 1420 for the user 1402.

In embodiments, different users can ambulate or move differently and the application of force or torque can affect gait in different ways. The user 1402 can perform a variety of different activities 1412, steady state and transient, while wearing a plurality of sensors and one or more exoskeleton boots 100. In embodiments, the user 1402 can be videotaped or recorded being in a motion capture system to generate video data and/or motion capture data associated with the activities 1412. The activities 1412 can include test conditions that apply torque or force to the user through the exoskeleton boot 100 to determine and learn how the specific user 1402 ambulates, moves and how a gait of the user is affected using the exoskeleton boot 100. In some embodiments, the test activities 1412 can include different power levels of the exoskeleton boots 100. For example, an ankle angle measurement may provide a first value when the exoskeleton boot 100 is unpowered and a second, different value when torque is applied via a powered exoskeleton boot 100. Thus, the user 1402 can perform activities 1412 and be measured in different positions (e.g., sitting, standing) when the exoskeleton boot 100 is unpowered and powered through different training cycles to better learn movement patterns of the user 1402 (e.g., cycle 1: unpowered data, cycle 2: imperfect powered data, cycle 3: better powered data). In embodiments, the test activities 1412 can include, but are not limited to, different types of gait (e.g., walking, running, jumping), different terrains (e.g., pavement, grass, sand, ice), different speeds (e.g., slow, medium, fast), and different power levels (e.g., high augmentation, transparent, low).

In some embodiments, the activity 1412 can include activities or movements performed in a simulator environment or using a simulator and the user can be connected to equipment operating as or mimicking the exoskeleton boot 100 (or exoskeleton device). The simulator environment can be used to test different toque profiles 1422, torque values 1428 and/or commands 1426 prior to providing the values to an exoskeleton boot 100. For example, a user can be connected to equipment that includes, but is not limited to, cables (e.g., Bowden cables), braces, motors, controllers and/or other types of devices or equipment capable of providing torque to one or more joints of the user. The controller 1410 can be connected to the simulator environment and the equipment of the simulator environment to generate and provide one or more torque profiles 1422 to one or more joints of a user through the equipment of the simulator environment. The controller 1410 can generate one or more commands 1426 indicating a torque profile 1422 and/or one or more torque values 1428 associated with a torque profile 1422 to provide a target level of torque to the joints of the user. In embodiments, the equipment of the simulator can provide force, torque and/or power to the lower limb of the user 1402 to augment the movement of the user 1402 during the activity 1412. The activity 1412 can include steady state activities or transient activities. The activity 1412 can vary and can include any type of movement or motion performed or executed by the user 1402 and/or any type of use of one or more muscles of the user 1402, for example, that may not involve motion (e.g., holding a position, standing).

Referring now to operation (1512), and in some embodiments, sensor data 1420 can be received by the controller 1410. The sensor data 1420 can be associated with or correspond to an activity 1412 of the exoskeleton boot 100 during a first time interval 1430. The sensor data 1420 can be received from one or more sensors coupled to (e.g., wirelessly coupled, directed connected) or that are components of the exoskeleton boot 100. The sensor data 1420 can include, but is not limited to, motion data, force data, torque data, temperature data, speed, gait transitions, angle measurements (e.g., of different joints of the user 1402).

The sensor data 1420 can include data corresponding to steady state activities 1412 or transient activities 1412. The sensor data 1420 can include any form of data associated with, corresponding to or generated in response one or more activities 1412 performed or executed by the user 1402 wearing the exoskeleton boot 100. For example, the sensor data 1420 can include data associated with a movement or motion performed or executed by the user 1402 and/or any type of use of one or more muscles of the user 1402, for example, that may not involve motion (e.g., holding a position, standing) while wearing the exoskeleton boot 100. In embodiments, the sensor data 1420 can include or correspond to data retrieved from or obtained from a video or recording of the activity 1412 performed by the user 1402. The controller 1410 can receive a video or recording of the user 1402 performing the activity 1412 and determine or obtain sensor data 1420 from the video data or motion capture data.

The historical data 1450 can include sensor data 1420 from a number of different types of people or users, for example, people of varying age, size, and/or ability. In some embodiments, the controller 1410 can receive or obtain historical video data 1450 and/or historical motion capture data 1450 from one or more users 1402 (e.g., same body profile, same activity 1412 performed, same genetic traits) similar to the respective user 1402 using the exoskeleton boot 100 to compare and/or determine sensor data 1420 for the user 1402. The sensor data 1420 from the one or more similar users 1402 can be used to determine an average or identify anomalies in the sensor data 1420 obtained from the user 1402 performing the activity 1412 while wearing the exoskeleton boot 100. For example, a command modelling system 1416 can receive historical video data associated with one or more users 1402 performing one or more physical activities 1412. In embodiments, the command modelling system 1416 can receive historical motion capture data that includes historical sensor data.

Referring now to operation (1514), and in some embodiments, one or more torque profiles 1422 can be identified. The controller 1410 can determine torque profiles 1422 corresponding to or based in part on the activities 1412 performed by the user wearing the exoskeleton boot 100 and the sensor data 1420 associated with the activities 1412. In embodiments, the controller 1410 or command modelling system 1416 can determine the one or more torque profiles 1422 corresponding to the one or more physical activities 1412 based on the historical video data. The torque profile 1422 can include or represent a level of torque or torque value 1428 for the exoskeleton boot 100 to apply or provide to the lower limb of the user during an activity 1412 to augment or aid the user 1402 in performing the activity 1412. In embodiments, the torque profile 1422 can include or represent a level of force for the exoskeleton boot 100 to apply or provide to the lower limb of the user during an activity 1412 to augment or aid the user 1402 in performing the activity 1412. The torque profile 1422 can include a series of torque values 1428 (or force values) for the exoskeleton boot 100 to apply or provide to the lower limb of the user during an activity 1412 to augment or aid the user 1402 at different points or stages in the respective activity 1412 in performing and completing the activity 1412. For example, the activity 1412, such as standing up and jumping, can include a series of movements and each movement (e.g., plant foot, flex ankle, begin standing up, straighten leg, jump) can include a different toque value 1428 (e.g., standing up, walking, jumping) that the exoskeleton applies to the lower limb of the user to augment the user 1402 in performing the respective movement and thus, completing the activity 1412.

The controller 1410 can determine the torque values 1428 to generate one or more torque profiles 1422 based in part on the received sensor data 1420 and/or historical data (e.g., historical video data, historical motion capture data) that represents or includes data identifying how much aid the user 1402 may have needed in performing similar activities 1412 or movements previously. In embodiments, the torque profile 1422 can include predictions or predicted torque values 1428 that are predicted using the sensor data 1420 from the user 1402 performing one or more activities 1412 (e.g., same activities, similar activities) and/or one or more other users 1402 performing one or more activities 1412.

The controller 1410 can execute a machine learning device 1414 to receive the sensor data 1420 and predict and generate the torque values 1428 and torque profiles 1422. The machine learning device 1414 can predict a needed or desired torque value 1428 to perform one or more activities 1412. For example, the sensor data 1420 can include data associated with the user 1402 or other users 1402 walking, running, flexing an ankle, flexing a knee or jumping. The sensor data 1420 can include conditions (e.g., environmental, user specific) that the activities 1412 were performed under such as, but not limited to, indoors, outside, in the rain, male user, female user, type of gait. The sensor data 1420 can include or correspond to historical video data of the user 1402 performing one or more activities 1412 and/or historical motion capture data of the user 1402 performing one or more activities 1412.

The machine learning device 1414 can receive the sensor data 1420 including the type of activities 1412 and conditions as inputs and, for example using a machine learning algorithm, generates outputs as predicted torque values 1428 for the user 1402 to augment the user 1402 performing one or more activities 1412 in the future under the same or different conditions. In some embodiments, the inputs can include user provided inputs. For example, an administrator or user can provide data to modify or aggregate with the sensor data 1420. The user provided inputs can include data associated with the user 1402 performing one or more activities 1412, user physical parameters, user measurements, and biometrics. The machine learning device 1414 can predict torque values 1428 to augment the user 1402 transitioning between different states (e.g., active to rest, steady state to transient) and transitioning between different gaits (e.g., walking to running).

Referring now to operation (1516), and in some embodiments, a visual indication 1440 can be provided, for example, through a display 1335. In embodiments, a command modelling system 1416 can provide the visual indication 1440 through a display 1335, for example, a display device (e.g., computing device, mobile device) of a user device or of the exoskeleton boot 100. In embodiments, the command modelling system 1416 can provide for display, via a display device 1335 communicatively coupled to the command modelling system 1416, the visual indication 1440 of the historical motion capture data. The command modelling system 1416 can provide for display, via a display device 1335 communicatively coupled to the command modelling system 1416, a visual indication 1440 of the historical motion capture data.

The visual indication 1440 can include a video of the user 1402 performing an activity 1412, an image of the user 1402 performing an activity 1412, a marker, menu, window or selectable content item provided through the display 1335. The visual indication 1440 can include a menu or listing of torque profiles 1422 available for selection through the display 1335 or user interface 1330 portion of the display 1335 (e.g., touch screen, selectable content items). The visual indication 1440 can be used to provide feedback to a user of the display 1335 and/or allow the user of the display 1335 to provide feedback to the controller 1410 and/or exoskeleton boot 100, such as but not limited to, a selection of at least one torque profile 1422. The feedback can be used to generate one or more torque profiles 1422 or modify one or more torque profiles 1422. The visual indication 1440 can generate an indication 1442 identifying input (e.g., a selection) by a user of the display 1335 and corresponding to feedback from the user. For example, responsive to an interaction (e.g., click on, touch, hover, selection), the visual indication 1440 can generate and transmit an indication 1442 identifying input provided by a user of the display 1335. In some embodiments, the indications 1442 can include user provided inputs. For example, an administrator or user can provide data to modify or aggregate with the sensor data 1420. The user provided inputs can include data associated with the user 1402 performing one or more activities 1412, user physical parameters, user measurements, and biometrics (e.g., heartrate, EMG data). The machine learning device 1414 can predict torque values 1428 to augment the user 1402 transitioning between different states (e.g., active to rest, steady state to transient) and transitioning between different gaits (e.g., walking to running).

Referring now to operation (1518), and in some embodiments, an indication 1442 can be received, for example, through an input device 1330 (e.g., user interface) coupled to the command modeling system. The indication 1442 can include or correspond to an interaction with the visual indication 1440 provided through the display 1335. In embodiments, the indication 1442 can include a selection of at least one torque profile 1422. In some embodiments, the indication 1442 can include data associated with one or more activities 1412 and/or associated with one or more users 1402. The command modelling system 1416 can receive, via a user interface 1330, an indication 1442 of a torque profile 1422 corresponding to the visual indication

1440 of the historical motion capture data. The command modelling system 1416 can receive, via a user interface 1330, an indication 1442 of a type of physical activity 1412 corresponding to the visual indication 1440 of the historical motion capture data. In embodiments, the controller 1410 can receive, via the user interface 1330, input from the user prior to a second time interval 1430. The indication 1442 and/or input can be used by the controller to modify the sensor data 1420 or can be aggregated with the sensor data 1420 to modify or update one or more torque profiles 1422.

In some embodiments, user input can be received or the indication 1442 can include user input. The controller 1410 can receive via the user interface user input from the user of the exoskeleton boot 100. The controller 1410 can provide or connect to an application executing on a client device or the exoskeleton boot 100 and provided through the user interface 1330. In embodiments, the application can include an interface 1330 to provide or modify sensor data 1420 and/or historical data 1450. In one embodiment, the application can include a torque tool to enter torque values and/or modify torque values 1428 including historical torque values 1428 for the user and stored or maintained in a memory 1404 of the controller 1410. The user input can include, but is not limited to, a modification or change to one or more sensor data values and/or historical data values. The user input can include a rating of how a previous activity 1412 felt to the user (e.g., last step felt good, last step felt off), a user rating (e.g., a rating score, 0-10 rating), a rating of how the exoskeleton boot 100 performed during a previous activity 1412, and/or a value indicating a rate of perceived exhaustion (RPE). In some embodiments, the application can provide or illustrate a graph of a torque profile 1422 having multiple data points with each data pint correspond to a relationship between at least one torque value 1428 and at least one joint angle. The data points can include selectable or interactive content and the user can interact with (e.g., drag, touch, select) the different data points to modify torque values 1428 and/or the torque profile 1422 (e.g., in real-time) and adjust how the exoskeleton boot 100 is performing and/or feels to the respective user during an activity 1412. The controller 1410 can receive the new or modified values and update a current or active torque value 1422 and/or torque profile 1422 provided to the user, for example, to modify a current or active torque provided to the user through the exoskeleton boot 100 in real-time. In embodiments, the controller 1410 can receive from the application the new or modified values and update at least one sensor data 1420 and/or historical data 1450 associated with the user. In some embodiments, the controller 1410 can use the modified sensor data 1420 and/or modified historical data 1450 to modify a torque profile 1422 for the user or generate a new torque profile 1422 for the user.

Referring now to operation (1520), and in some embodiments, a model 1424 can be trained. The controller 1410, for example through the command modelling system 1416, can generate and train the model 1424 by providing the received sensor data 1420, historical data 1450, one or more indications 1442, one or more torque profiles 1422 and/or other forms of input as inputs to the model 1424 and execute the model 1424. In embodiments, the received sensor data 1420, historical data 1450, one or more indications 1442, one or more torque profiles 1422 and/or other forms of input as inputs can include or correspond to training data provided to the model 1424 and machine learning device 1414 to train the model 1424 to predict outputs, here commands 1426 to instruct the exoskeleton boot 100. The model 1424 can include the machine learning device 1414 (e.g., machine learning engine) and a machine learning algorithm such that as more and more inputs are received and provided to the model 1424, the model 1424 can be trained to predict torque values 1428 and torque profiles 1422 and generate one or more commands 1426 corresponding to the torque values 1428 and torque profiles 1422. The machine learning device 1414 can identify patterns or similarities between different data points of the received input and map the inputs to outputs that correspond to the identified patterns (e.g., ankle angle data, torque used to transition between walking and running in previous activities). The model 1424 can generate the commands 1426 based in part on the identified patterns in the received input data.

In embodiments, the torque profiles 1422 can be used as inputs into the model 1424 and to train the model 1424 to generate outputs corresponding to the commands 1426. The commands 1426 can include instructions provided to one or more components of the exoskeleton boot 100 to generate a torque profile 1422 or a torque value 1428 of a series of torque values 1428 forming a torque profile 1422. For example, the command modelling system 1416 can train, using the machine learning technique (e.g., machine learning device 1414) and based on the one or more torque profiles 1422, the model 1424 to cause the model 1424 to output the one or more commands 1426 responsive to the sensor data 1420. The command modelling system 1416 can train, using the machine learning technique and based on the indication 1442 of the torque profile 1422 received via the user interface 1330, the model 1424 to cause the model 1424 to output the one or more commands 1426 responsive to the sensor data 1420. The command modelling system 1416 can train, using the machine learning technique and based on the indication 1442 of the type of physical activity 1412 received via the user interface 1330, the model 1424 to cause the model 1424 to output the one or more commands 1426 responsive to the sensor data.

Referring now to operation (1522), and in some embodiments, one or more commands 1426 can be determined. The controller 1410 can determine, based on the sensor data 1420 input into the model 1424 trained via a machine learning technique based on historical motion capture data 1420 associated with one or more users 1402 performing one or more physical activities 1412, one or more commands 1426 for a second time interval 1430 subsequent to the first time interval 1430. The controller 230 can obtain or receive the commands 1426 generated by the model 1424 for a subsequent activity 1412 to be performed by the user 1402 during the second time interval 1430. In embodiments, the controller 1410 can select one or more commands 1426 from a plurality of commands 1426 generated by the model 1424 based in part on an identified activity 1412 to be performed by the user 1402 wearing the exoskeleton boot 100 during the second time interval 1430. The commands 1426 can include or correspond to one or more torque profiles 1422 to be provided to the exoskeleton boot 100 that include torque values 1428 for the exoskeleton boot 100 to apply to a lower limb of the user 1402 to augment or aid the user 1402 in performing the subsequent or next activity 1412. The commands 1426 can include or correspond to instructions to control a torque, force, velocity or any combination of torque, force and velocity (e.g., impedance) applied to a lower limb of the user 1402 via the exoskeleton boot 100. The commands 1426 can include or correspond to instructions to set a target level of torque, force, velocity or any combination of torque, force and velocity (e.g., impedance) to be applied to a lower limb of the user 1402 via the exoskeleton boot 100. The controller 1410 can determine the one or more commands 1426 for the second time interval 1430 to match a torque profile 1422 selected based on the sensor data 1420 via the model 1424. In embodiments, the controller 1410 can generate, via the model 1424, the one or more commands 1426 based on the input (e.g., indications 1442, user input) and the sensor data 1420.

Referring now to operation (1524), and in some embodiments, the one or more commands 1426 can be transmitted. For example, the controller 1410 can transmit the one or more commands 1426 generated based on the model 1424 to the electric motor 330 to cause the electric motor 330 to generate torque about the axis of the rotation of the ankle joint of the user 1402 in the second time interval 1430. The electric motor 330 can generate torque corresponding to a torque profile 1422 and/or torque values 1428 identified in the one or more commands 1426 to cause the exoskeleton boot 100 to apply a force to a lower limb of the user 1402 to augment or aid the user 1402 in performing the subsequent or next activity 1412.

Referring now to operation (1526), and in some embodiments, a subsequent activity 1412 can be performed using the exoskeleton boot 100. In embodiments, the exoskeleton boot 100 can provide force, torque and/or power to the lower limb of the user 1402 the exoskeleton boot 100 is coupled to with to augment the movement of the user 1402 during the activity 1412 using the one or more commands 1426. In embodiments, the subsequent activity 1412 can include a new activity 1412 or a continuation of the first activity 1412 (e.g., second portion of initial activity). The exoskeleton boot 100 can transfer energy to the lower limb of the user 1402, based on the one or more commands 1426 and torque profiles 1422 generated for the user 1402, to augment the movement of the user 1402 during the activity 1412. The exoskeleton boot 100 can reduce a difficulty of performing the respective activity 1412 or multiple activities 1412 by reducing the energy or effort the user 1402 exerts to perform the respective activity 1412. In some embodiments, the method 1500 can return to operation (1512) to monitor for or wait for subsequent sensor data 1420 associated with the subsequent activity 1412. The controller 1410 can continue to monitor one or more activities 1412 performed by the user 1402 wearing the exoskeleton boot 100 and obtain sensor data 1420 associated with the one or more activities 1412 to generate more accurate commands 1426 and torque profiles 1422 for the user 1402. For example, as the user performs additional activities 1412 using the exoskeleton boot 100, the controller 1410 can provide sensor data 1420 associated with the additional activities 1412 to the model 1424 to further train and refine the predictions and commands 1426 generated using the model 1424 to provide a more customized user experience for the respective user 1402 using the exoskeleton boot 100.

Figure 16:
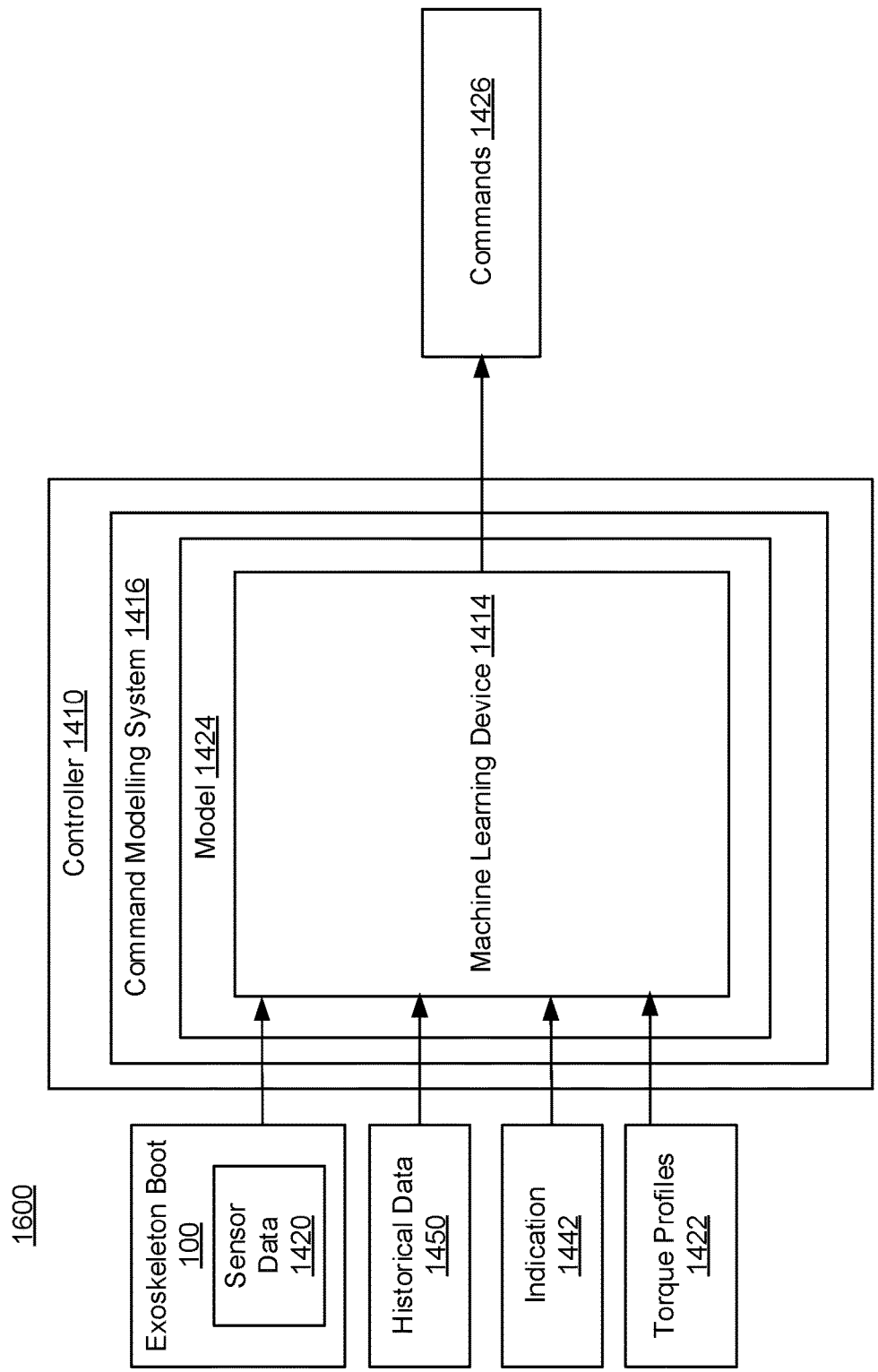
FIG. 16 is a block diagram of a system for training a model to generate one or more commands in accordance with an illustrative embodiment.

FIG. 16 is a block diagram of a system 1600 for training a model to generate one or more commands in accordance with an illustrative embodiment. In embodiments, the model 1424 can be trained using different data points (e.g., inputs) to predict and determine commands 1426 to control, for example, operation and use of an exoskeleton boot 100. The command modelling system 1416 of the controller 1410 can receive the inputs and provide the inputs to the model 1424 to train the model 1424 for one or more users 1402 of the exoskeleton device 100. The model 1424 can include a machine learning device 1414 to execute one or more machine learning algorithms 1414 and/or artificial intelligence (AI) engines to turn the received inputs into a model and one or more predictions for generating commands 1426.

The inputs can include but is not limited to, sensor data 1420, historical data 1450, indications 1442 and one or more torque profiles 1422. The inputs can include sensor data 1420 associated with a plurality of users 1402 of varying ages, sizes and ability levels or users 1402 in a similar age range, size range and/ability range as a current user 1402 of the exoskeleton boot 100. The inputs can include sensor data 1420 associated with a plurality of different types of activities, states (e.g., transient state, steady state) and/or power levels (e.g., unpowered, low power level, full power level) to learn and train the model 1424 across a variety of different movement patterns.

The command modelling system 1416 can provide one or more of the sensor data 1420, historical data 1450, indications 1442 and one or more torque profiles 1422 to execute and train the model 1424 at a time. In some embodiments, the command modelling system 1416 can continually provide one or more of the sensor data 1420, historical data 1450, indications 1442 and one or more torque profiles 1422 to execute and train the model 1424, for example, during a series of activities 1412 to update the model 1424 and generate new subsequent commands 1426 as a user 1402 transitions between the different activities 1412 in the series of activities 1412.

The sensor data 1420 can include real-time sensor data, for example, received as the user 1402 is performing an activity 1412 to enable the model 1424 to be trained using real-time data and generate commands 1426 using the real-time sensor data 1420. In embodiments, the users 1402 can wear the exoskeleton boots 100 and the controller 1410, through the model 1424, ca provide real-time optimization to alter commands 1426 or generate new commands 1426 to reach a desired torque profile 1422. In some embodiments, the user 1402 can provide real-time feedback to the controller 1410 and model 1424, for example, through selection of a torque profile 1422 (e.g., indication 1442) via a user interface 1330 and alter the users own respective torque profile 1422 in real-time.

The command modelling system 1416 can receive historical data 1450 from one or more users 1402 to provide a larger data set to train the model 1424. For example, the command modelling system 1416 can provide historical sensor data 1450 from different users 1402 to provide a variety of different data points that include information on various conditions (e.g., environmental) and different type of users 1402 and generate an increased level of training data to train the model 1424 initially prior a respective user 1402 generating a determined amount of sensor data 1420 on their own.

The model 1424 can process the received inputs using the machine learning device 1414 to apply one or more machine learning algorithms and/or AI techniques to the received inputs and generate commands 1426 for instructing and controlling the exoskeleton boot 100. For example, the model 1424 can be trained to predict torque values 1428 and torque profiles 1422 and generate one or more commands 1426 corresponding to the torque values 1428 and torque profiles 1422. The machine learning device 1414 can identify patterns or similarities between different data points of the received input. The machine learning device 1414 can train the model 1424 to predict how the application of a particular level of torque, force and/or velocity can impact the movement, gait and/or performance of the user 1402 performing one or more activities 1412. In some embodiments, the machine learning device 1414 can, for example using AI, map or determine relationships between changes in sensor data 1420 (e.g., changes in sensor readings)

responsive to different levels of torque, force and/or velocity provided to a lower limb of a user 1402 through the exoskeleton boot 100 to predict how the user 1402 may react to a determined levels of torque, force and/or velocity in one or more current activities 1412 or future activities 1412. For example, the machine learning device 1414 can learn or identify patterns of a torque trajectory based in part on provided sensor data 1420 (e.g., powered data, unpowered data). The model 1424 can generate commands 1426 to apply torque through at least one exoskeleton boot 100 to a lower limb of the user 1402. The model 1424 can receive subsequent or follow-up sensor data 1420 associated with the user 1402 performing activities 1412 using the exoskeleton boot 100 using the commands 1426. The machine learning device 1414 can characterize the subsequent sensor data 1420 to determine, for example, if a current level of torque is sufficient or if a previously applied torque met the respective user's 1402 needs to perform the activity 1412. The machine learning device 1414 can use the characterization to further train and update the model 1424, for example, for one or more subsequent activities 1412 performed by the user 1402.

The commands 1426 can include instructions provided to one or more components of the exoskeleton boot 100 to generate a torque profile 1422 or a torque value 1428 of a series of torque values 1428 forming a torque profile 1422. The controller 1410 can determine, based on the sensor data 1420 input into the model 1424 trained via a machine learning technique based on historical motion capture data 1420 associated with one or more users 1402 performing one or more physical activities 1412, one or more commands 1426 for a second time interval 1430 subsequent to the first time interval 1430. The model 1424 can generate the commands 1426 based in part on an activity 1412 the user 1402 is performing or is about to perform. For example, different activities 1412 can include different commands 1426 to augment a particular motion or movement of the user 1402 during the respective activity 1412. The commands 1426 can include or correspond to one or more torque profiles 1422 to be provided to the exoskeleton boot 100 that include torque values 1428 for the exoskeleton boot 100 to apply to a lower limb of the user 1402 to augment or aid the user 1402 in performing the subsequent or next activity 1412.

Embodiments of the subject matter and the operations described in this specification can be implemented in digital electronic circuitry, or in computer software, firmware, or hardware, including the structures disclosed in this specification and their structural equivalents, or in combinations of one or more of them. The subject matter described in this specification can be implemented as one or more computer programs, e.g., one or more circuits of computer program instructions, encoded on one or more computer storage media for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate components or media (e.g., multiple CDs, disks, or other storage devices).

The operations described in this specification can be performed by a data processing apparatus on data stored on one or more computer-readable storage devices or received from other sources. The term "data processing apparatus" or "computing device" encompasses various apparatuses, devices, and machines for processing data, including by way of example a programmable processor, a computer, a system on a chip, or multiple ones, or combinations of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a circuit, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more circuits, subprograms, or portions of code). A computer program can be deployed to be executed on one computer or on multiple computers that are located at one site or distributed across multiple sites and interconnected by a communication network.

Processors suitable for the execution of a computer program include, by way of example, microprocessors, and any one or more processors of a digital computer. A processor can receive instructions and data from a read only memory or a random access memory or both. The elements of a computer are a processor for performing actions in accordance with instructions and one or more memory devices for storing instructions and data. A computer can include, or be operatively coupled to receive data from or transfer data to, or both, one or more mass storage devices for storing data, e.g., magnetic, magneto optical disks, or optical disks. A computer need not have such devices. Moreover, a computer can be embedded in another device, e.g., a personal digital assistant (PDA), a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The implementations described herein can be implemented in any of numerous ways including, for example, using hardware, software or a combination thereof. When implemented in software, the software code can be executed on any suitable processor or collection of processors, whether provided in a single computer or distributed among multiple computers.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

A computer employed to implement at least a portion of the functionality described herein may comprise a memory, one or more processing units (also referred to herein simply as "processors"), one or more communication interfaces, one or more display units, and one or more user input devices. The memory may comprise any computer-readable media, and may store computer instructions (also referred to herein as "processor-executable instructions") for implementing the various functionalities described herein. The processing unit(s) may be used to execute the instructions. The communication interface(s) may be coupled to a wired or wireless network, bus, or other communication means and may therefore allow the computer to transmit communications to or receive communications from other devices. The display unit(s) may be provided, for example, to allow a user to view various information in connection with execution of the instructions. The user input device(s) may be provided, for example, to allow the user to make manual adjustments, make selections, enter data or various other information, or interact in any of a variety of manners with the processor during execution of the instructions.

The various methods or processes outlined herein may be coded as software that is executable on one or more processors that employ any one of a variety of operating systems or platforms. Additionally, such software may be written using any of a number of suitable programming languages or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the solution discussed above. The computer readable medium or media can be transportable, such that the program or programs stored thereon can be loaded onto one or more different computers or other processors to implement various aspects of the present solution as discussed above.

The terms "program" or "software" are used herein to refer to any type of computer code or set of computer-executable instructions that can be employed to program a computer or other processor to implement various aspects of embodiments as discussed above. One or more computer programs that when executed perform methods of the present solution need not reside on a single computer or processor, but may be distributed in a modular fashion amongst a number of different computers or processors to implement various aspects of the present solution.

Computer-executable instructions may be in many forms, such as program modules, executed by one or more computers or other devices. Program modules can include routines, programs, objects, components, data structures, or other components that perform particular tasks or implement particular abstract data types. The functionality of the program modules can be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Any references to implementations or elements or acts of the systems and methods herein referred to in the singular can include implementations including a plurality of these elements, and any references in plural to any implementation or element or act herein can include implementations including only a single element. References in the singular or plural form are not intended to limit the presently disclosed systems or methods, their components, acts, or elements to single or plural configurations. References to any act or element being based on any information, act or element may include implementations where the act or element is based at least in part on any information, act, or element.

Any implementation disclosed herein may be combined with any other implementation, and references to "an implementation," "some implementations," "an alternate implementation," "various implementations," "one implementation" or the like are not necessarily mutually exclusive and are intended to indicate that a particular feature, structure, or characteristic described in connection with the implementation may be included in at least one implementation. Such terms as used herein are not necessarily all referring to the same implementation. Any implementation may be combined with any other implementation, inclusively or exclusively, in any manner consistent with the aspects and implementations disclosed herein.

References to "or" may be construed as inclusive so that any terms described using "or" may indicate any of a single, more than one, and all of the described terms. References to at least one of a conjunctive list of terms may be construed as an inclusive OR to indicate any of a single, more than one, and all of the described terms. For example, a reference to "at least one of 'A' and 'B'" can include only 'A', only 'B', as well as both 'A' and 'B'. Elements other than 'A' and 'B' can also be included.

The systems and methods described herein may be embodied in other specific forms without departing from the characteristics thereof. The foregoing implementations are illustrative rather than limiting of the described systems and methods.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed is:

1. A system to augment motion via an exoskeleton of a foot-ankle, comprising:
   a shin pad of a foot-ankle exoskeleton configured to couple to a shin of a user below a knee of the user;
   an actuator located below the knee of the user and coupled to the shin pad, the actuator configured to generate torque about an axis of rotation of an ankle joint of the user; and
   a controller, comprising memory and one or more processors, to:
   receive sensor data associated with activity of the exoskeleton during a first time interval;
   input the sensor data into a model trained via a machine learning technique using historical motion data associated with one or more users performing one or more physical activities;
   generate a set of candidate parameters from a candidate torque profile based on the sensor data input into the model;
   modify the model based on a comparison of the set of candidate parameters and a set of target parameters generated from a target torque profile generated prior to receipt of the sensor data;
   determine, for a second time interval subsequent to the first time interval, one or more commands to match the set of candidate parameters; and
   transmit the one or more commands generated based on the model to the actuator to cause the actuator to generate torque about the axis of rotation of the ankle joint of the user in the second time interval.

2. The system of claim 1, comprising:
   a battery holder coupled to the shin pad, the battery holder to receive a battery module configured to provide power to at least one of the controller or the actuator.

3. The system of claim 1, comprising:
   a housing enclosing the actuator, the housing located below the knee of the user and coupled to the shin pad; and
   an output shaft coupled to the actuator and extending through a bore in the housing.

4. The system of claim 1, comprising:
   a housing that encloses the controller, the housing located below the knee of the user and coupled to the shin pad.

5. The system of claim 1, comprising:
   one or more housings that enclose the controller and the actuator, the one or more housings located below the knee of the user and coupled to the shin pad.

6. The system of claim 1, wherein the controller is further configured to:
   generate a candidate trajectory based on the set of candidate parameters; and
   generate a target trajectory based on the set of target parameters.

7. The system of claim 1, wherein the controller is further configured to:
   select the set of candidate parameters based on the sensor data into the model.

8. The system of claim 1, wherein the historical motion data corresponds to data collected via the exoskeleton in a plurality of states, the plurality of states comprising at least one of an unpowered state, a partially powered state, or a fully powered state.

9. The system of claim 1, wherein the controller is further configured to:
   receive, via a network, the model from a command modelling system that trains the model based on the historical motion data, wherein the command modelling system:
   receives the historical motion data comprising historical sensor data;
   provides, for display via a display device communicatively coupled to the command modelling system, a visual indication of the historical motion data;
   receives, via a user interface, an indication of the candidate torque profile corresponding to the visual indication of the historical motion data; and
   train, using the machine learning technique and based on the indication of the candidate torque profile received via the user interface, the model to cause the model to output the one or more commands responsive to the sensor data.

10. The system of claim 1, wherein:
    the historical motion data comprises at least one of inertial measurement unit data, goniometer data, infrared reflector data, or force plate data; and
    the sensor data comprises at least one of ankle joint data, inertial measurement unit data, or battery data.

11. A method of augmenting motion via an exoskeleton of a foot-ankle, comprising:
    receiving, by a controller comprising memory and one or more processors, sensor data associated with activity of a foot-ankle exoskeleton during a first time interval;
    inputting, by the controller, the sensor data into a model trained via a machine learning technique using historical motion data associated with one or more users performing one or more physical activities;

generating, by the controller, a set of candidate parameters from a candidate torque profile based on the sensor data input into the model;

modifying, by the controller, the model based on a comparison of the set of candidate parameters and a set of target parameters generated from a target torque profile generated prior to receipt of the sensor data;

determining, by the controller, for a second time interval subsequent to the first time interval, one or more commands to match the set of candidate parameters; and transmitting, by the controller, the one or more commands generated based on the model to an actuator to cause the actuator to generate torque about an axis of rotation of an ankle joint of a user in the second time interval, wherein the actuator is located below a knee of the user and coupled to a shin pad of the exoskeleton, and the shin pad couples to a shin of the user below the knee of the user.

12. The method of claim 11, comprising:
generating, by the controller, a candidate trajectory based on the set of candidate parameters; and
generating, by the controller, a target trajectory based on the set of target parameters.

13. The method of claim 11, comprising:
selecting, by the controller, the set of candidate parameters based on the sensor data into the model.

14. The method of claim 11, comprising:
receiving, by the controller via a network, the model from a command modelling system that trains the model based on the historical motion data, wherein the command modelling system:
receives the historical motion data comprising historical sensor data;
provides, for display via a display device communicatively coupled to the command modelling system, a visual indication of the historical motion data;
receives, via a user interface, an indication of the candidate torque profile corresponding to the visual indication of the historical motion data; and
train, using the machine learning technique and based on the indication of the candidate torque profile received via the user interface, the model to cause the model to output the one or more commands responsive to the sensor data.

15. A method, comprising:
providing a shin pad of a foot-ankle exoskeleton to couple to a shin of a user below a knee of the user;
providing an actuator located below the knee of the user and coupled to the shin pad, the actuator configured to generate torque about an axis of rotation of an ankle joint of the user; and
providing a controller, comprising memory and one or more processors, the controller configured to:
receive sensor data associated with activity of the exoskeleton during a first time interval;
input the sensor data into a model trained via a machine learning technique using historical motion data associated with one or more users performing one or more physical activities;
generate a set of candidate parameters from a candidate torque profile based on the sensor data input into the model;
modify the model based on a comparison of the set of candidate parameters and a set of target parameters generated from a target torque profile generated prior to receipt of the sensor data;
determine, for a second time interval subsequent to the first time interval, one or more commands to match the set of candidate parameters; and
transmit the one or more commands generated based on the model to the actuator to cause the actuator to generate torque about the axis of rotation of the ankle joint of the user in the second time interval.

16. The method of claim 15, comprising:
providing a battery holder coupled to the shin pad, the battery holder to receive a battery module configured to provide power to at least one of the controller or the actuator.

17. The method of claim 15, comprising:
providing a housing enclosing the actuator, the housing located below the knee of the user and coupled to the shin pad; and
providing an output shaft coupled to the actuator and extending through a bore in the housing.

18. The method of claim 15, comprising:
providing a housing that encloses the controller, the housing located below the knee of the user and coupled to the shin pad.

* * * * *